United States Patent [19]
Iinuma

[11] Patent Number: 5,551,434
[45] Date of Patent: Sep. 3, 1996

[54] ULTRASONIC IMAGING DIAGNOSIS APPARATUS

[75] Inventor: Kazuhiro Iinuma, Tochigi-ken, Japan

[73] Assignee: Kabushiki Kaisha Toshiba, Kawasaki, Japan

[21] Appl. No.: 492,633

[22] Filed: Jun. 20, 1995

[30] Foreign Application Priority Data

Jun. 22, 1994 [JP] Japan .................................. 6-140347
Jun. 22, 1994 [JP] Japan .................................. 6-140348

[51] Int. Cl.$^6$ ...................................................... A61B 8/00
[52] U.S. Cl. ...................................................... 128/661.09
[58] Field of Search ......................... 128/660.05, 660.07, 128/661.08, 661.09, 661.10, 662.01

[56] References Cited

U.S. PATENT DOCUMENTS

| | | | |
|---|---|---|---|
| 4,790,322 | 12/1988 | Iinuma . | |
| 5,148,808 | 9/1992 | Satake | 128/660.05 |
| 5,170,792 | 12/1992 | Sturgill et al. | 128/661.08 |
| 5,211,169 | 5/1993 | Freeland | 128/661.08 |
| 5,329,929 | 7/1994 | Sato et al. | 128/660.05 |
| 5,425,365 | 6/1995 | Iinuma | 128/660.05 |

*Primary Examiner*—George Manuel
*Attorney, Agent, or Firm*—Finnegan, Henderson, Farabow, Garrett & Dunner, L.L.P.

[57] ABSTRACT

A probe set in contact with a subject under examination emits ultrasonic waves, scanning a sectional plane of the subject. The probe receives the waves reflected from the sectional plane, thereby acquiring tomography data and velocity data. Frames of tomography data and frames of velocity data are stored. After completion of the scanning, a tomography image of the sectional plane is reproduced from the tomography data and is displayed. An operator sets a region of interest (ROI) on the tomography image displayed. A blood flow velocity distribution, a blood stream volume or a tissue velocity distribution is calculated from the velocity data corresponding to the ROI. That is, the operator can devote himself to an operation of fitting the scanning plane of the probe to an optimum sectional plane of the body during a scan and to an operation of setting the ROI in an optimum position while tomography images are being reproduced. In other words, the operator is relieved of the burden of performing the probe operation and the ROI setting operation simultaneously. Thus, it becomes easy to fit the scanning plane to the optimum plane and to set the ROI in the optimum position.

13 Claims, 16 Drawing Sheets

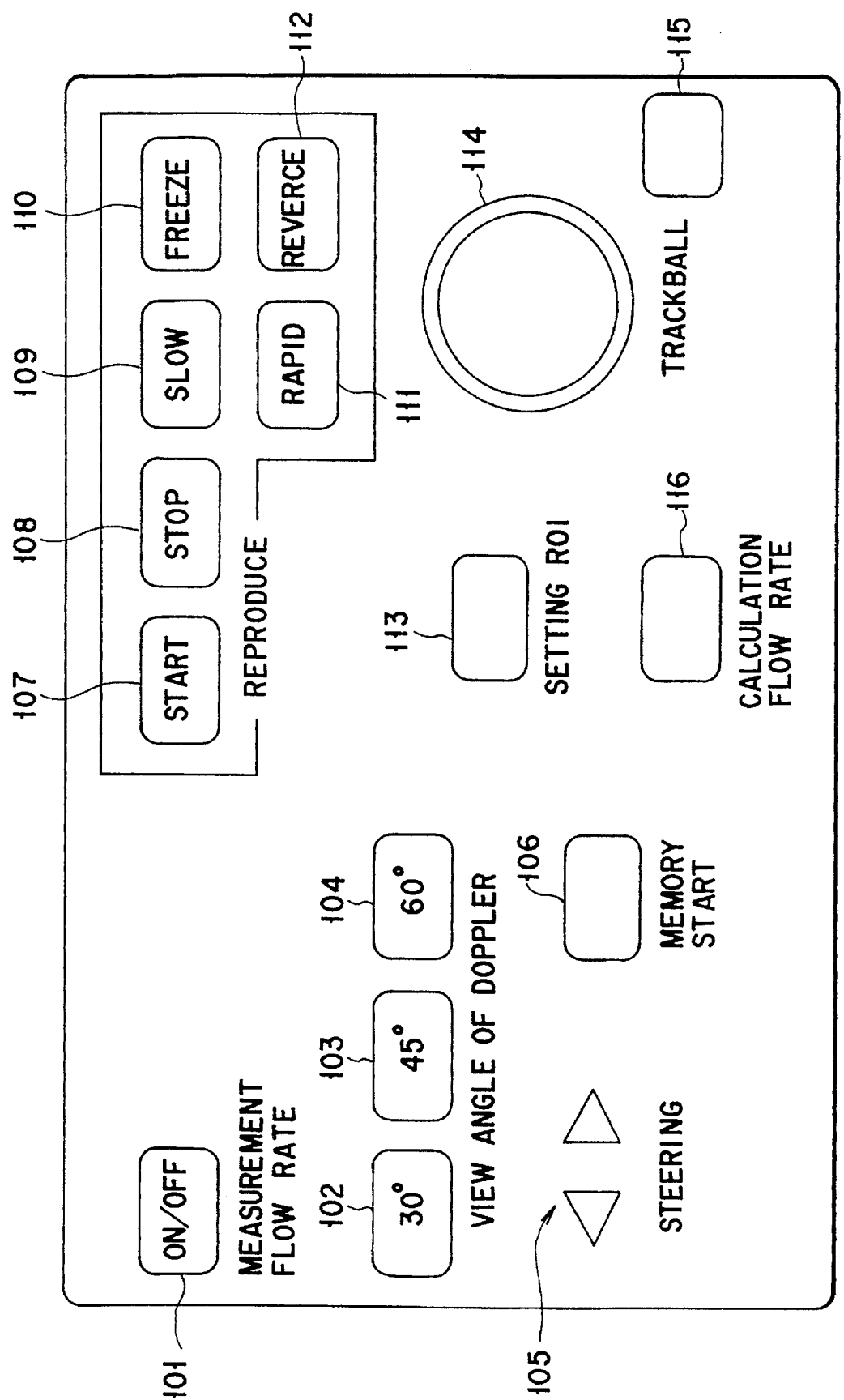
F I G. 2

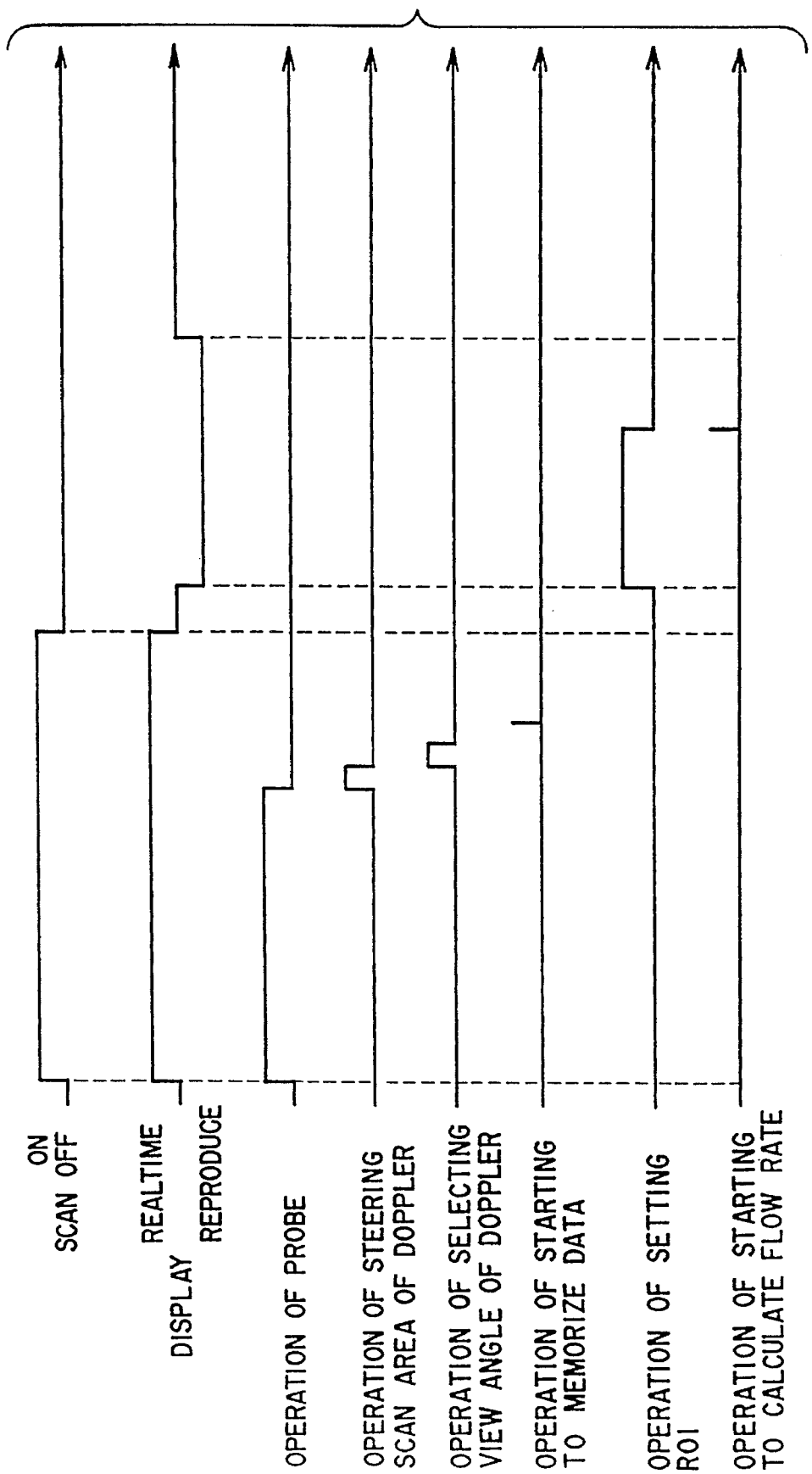

ULTRASONIC IMAGING DIAGNOSIS APPARATUS

BACKGROUND OF THE INVENTION

1. Field of the Invention

The present invention relates to an ultrasonic imaging diagnosis apparatus which can provide tissue images, blood flow rate data and blood-flow images of human bodies under examination.

2. Description of the Related Art

To make a diagnosis of circulatory organs, it is important to measure a blood flow rate, to observe the motion of the cardiac muscle and the flow of the blood particularly a cardiac output indicating blood flow discharged from the heart to the whole body via the aorta. Conventionally various measuring methods have been proposed. The ultrasonic imaging method is the best of those used, because it is noninvasive and simple. With this method, ultrasonic beams are emitted in multiple directions, the blood flow velocity is obtained from phase information of reflected waves, and the blood flow rate is obtained from the blood flow velocity.

However, the blood flow measurement method using ultrasonic waves has two factors that lower the measurement accuracy. Consider the case of measurement of a cardiac output. Suppose that a sector scan which is suitable for examination of hearts is used.

First, the first factor will be described. The doctor puts an ultrasonic probe to the chest wall of a human body under examination and changes the angle and position of the probe relative to the chest wall while watching a tomography image in real time so as to fit the scanning plane of the probe to an optimum sectional plane taken through the lengthwise dimension of the outflow tract of the heart. The tomography image along this scanning plane is displayed in real time on a TV monitor. The doctor then operates a mouse or trackball to set up a line of interest or a region of interest (hereinafter referred to simply as a line of interest) in an optimum position on the tomography image so that it will cross the outflow tract. Finally, the doctor instructs the CPU in the imaging apparatus to start calculation of the blood flow rate.

By the way, the angle and position that the probe takes relative to the chest wall must be adjusted with high accuracy. This is because even if the angle and position of the probe are changed slightly, the scanning plane will deviate from the optimum sectional plane. Thus, the doctor must concentrate on adjusting the probe so that its scanning plane will not deviate from the optimum sectional plane until the measurement is terminated. Under such condition, it is very difficult for the doctor to perform the operation of setting the line of interest. If the scanning plane deviates from the optimum sectional plane, the line of interest cannot be placed accurately in the desired position, which will result in reduced accuracy of blood flow measurement.

The second factor will be described next. A two-dimensional scan in the Doppler mode for blood flow measurement is made as follows. First, the transmission/reception of ultrasonic waves is performed for a first scanning line. The transmission/reception of ultrasonic waves for the first scanning line is repeated at least twice, normally 16 times. After the transmission/reception of ultrasonic waves is successively repeated 16 times for the first scanning line, the same operation is performed for the next scanning line. A one-frame scan is completed by repeating the transmission of ultrasonic waves 16 times for the same scanning line and shifting the ultrasound transmission path from each scanning line to the next adjacent scanning line.

Therefore, there is some difference in actual data acquisition time between each scanning line and the next adjacent scanning line. Suppose, for example, that the repetition period is 200 μs, the number of times the transmission of ultrasonic waves is repeated for the same scanning line is 16, and the number of scanning lines for one frame is eight. Then, a time difference between two adjacent scanning lines will be $$200\ \mu s \times 16 = 3.2\ ms$$

The time difference between the first transmission of the first scanning line and the sixteenth transmission of the last scanning line in one scan will be $$200\ \mu s \times 16 \times 8 = 25.6\ ms$$

The blood flow rate is given by integrating the flow velocity at points on the cross section of a blood vessel. Thus, the time difference between scanning lines will produce an error in the blood flow rate instantaneously obtained. That is, the blood flow rate will be measured as an integration value of flow velocities measured at different times, which results in a reduction in measurement accuracy. Further, the time difference will make it somewhat difficult to observe the motion of the cardiac muscle and the flow of the blood.

SUMMARY OF THE INVENTION

An object of the present invention is to provide an ultrasonic diagnosis apparatus which serves to detect a blood flow rate, blood flow velocity profile or a tissue velocity with high accuracy.

Another object of the invention is to provide an ultrasonic diagnosis apparatus which can accomplish reliable observation of the motion of the cardiac muscle and the flow of blood despite the errors resulting from the time difference occurring during the observation.

According to a first aspect of the present invention there is provided an ultrasonic imaging apparatus comprising: a probe to be set in contact with a subject under examination, for transmitting ultrasonic waves and receiving reflected waves; scanning means for driving the probe to scan a sectional plane of the subject with an ultrasonic beam; means for obtaining tomography data from an output of the scanning means; means for obtaining velocity data from the output of the scanning means; first storage means for storing multiple frames of the tomography data; second storage means for storing multiple frames of the velocity data; display means for displaying the tomography data stored in the storage means in the form of a tomography image after the scanning means finishes scanning the sectional plane; operating means for setting a region of interest (ROI) on the tomography image displayed by the display means; and means for calculating, for each frame, a distribution of blood flow velocity, a blood flow rate or a tissue velocity from each frame from the velocity data stored in the second storage means and corresponding to the ROI.

According to a second aspect of the present invention there is provided an ultrasonic imaging apparatus comprising: a probe for transmitting ultrasonic waves and receiving reflected waves; scanning means for driving the probe to scan a sectional plane of a subject under examination, with an ultrasonic beam; calculation means for calculating reflected wave data for each of sampling points in a sectional plane of the subject, from an output of the scanning means; storage means for storing at least two frames of the reflected wave data; estimation means for estimating reflected wave data equivalent to reflected wave data acquired by scanning simultaneously all sampling points, from the reflected wave data stored in the storage means; means for calculating a blood flow rate from the reflected wave data estimated by the estimation means; and display means for displaying at least one of the blood flow rate and a two dimensional image, the two dimensional image being obtained from the reflected wave data by the estimation means.

According to the first aspect, the following advantages are obtained. An operator can to set an ROI while reproducing tomography images. That is, the operator can to devote himself to an operation of fitting the scanning plane of the probe to an optimum sectional plane of the body during a scan and to an operation of setting the ROI in an optimum position while tomography images are being reproduced. In other words, the operator is relieved of the burden of performing the probe operation and the ROI setting operation simultaneously. Thus, it becomes easy to fit the scanning plane to the optimum plane and to set the ROI in the optimum position. This will improve the flow rate measurement accuracy.

According to the second aspect, the following advantage is obtained. Equivalent blood flow rate and equivalent two-dimensional images can be obtained by scanning all the sampling points simultaneously. Thus, the flow rate measurement accuracy is improved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 2 is a plan view of the console of FIG. 1;

FIG. 4 is a timing diagram for use in explanation of the operation of the first embodiment;

DETAILED DESCRIPTION OF THE PREFERRED EMBODIMENTS

Hereinafter the preferred embodiments of the present invention will be described with reference to the accompanying drawings.

First, some blood-flow-related terms treated herein will be defined briefly.

The instantaneous flow rate refers to the total blood flow through a region of interest (ROI) during a very short period of time, which is obtained by integrating the blood flow velocity for each small area over the cross section of a blood vessel. Hereinafter, the instantaneous flow rate is referred simply to as the flow rate. When a region of interest is set in an outflow tract, the flow rate is obtained as the rate of outflow, while, when it is set in an inflow tract, the flow rate is obtained as the rate of inflow.

The single stroke volume refers to the blood flow discharged from a ventricle by a single heart stroke, which is obtained by integrating the rate of inflow or outflow over one heart-stroke period.

The cardiac output refers to the blood flow discharged from the ventricle, which is obtained by multiplying the single stroke volume and the heart rate.

Figure 1:
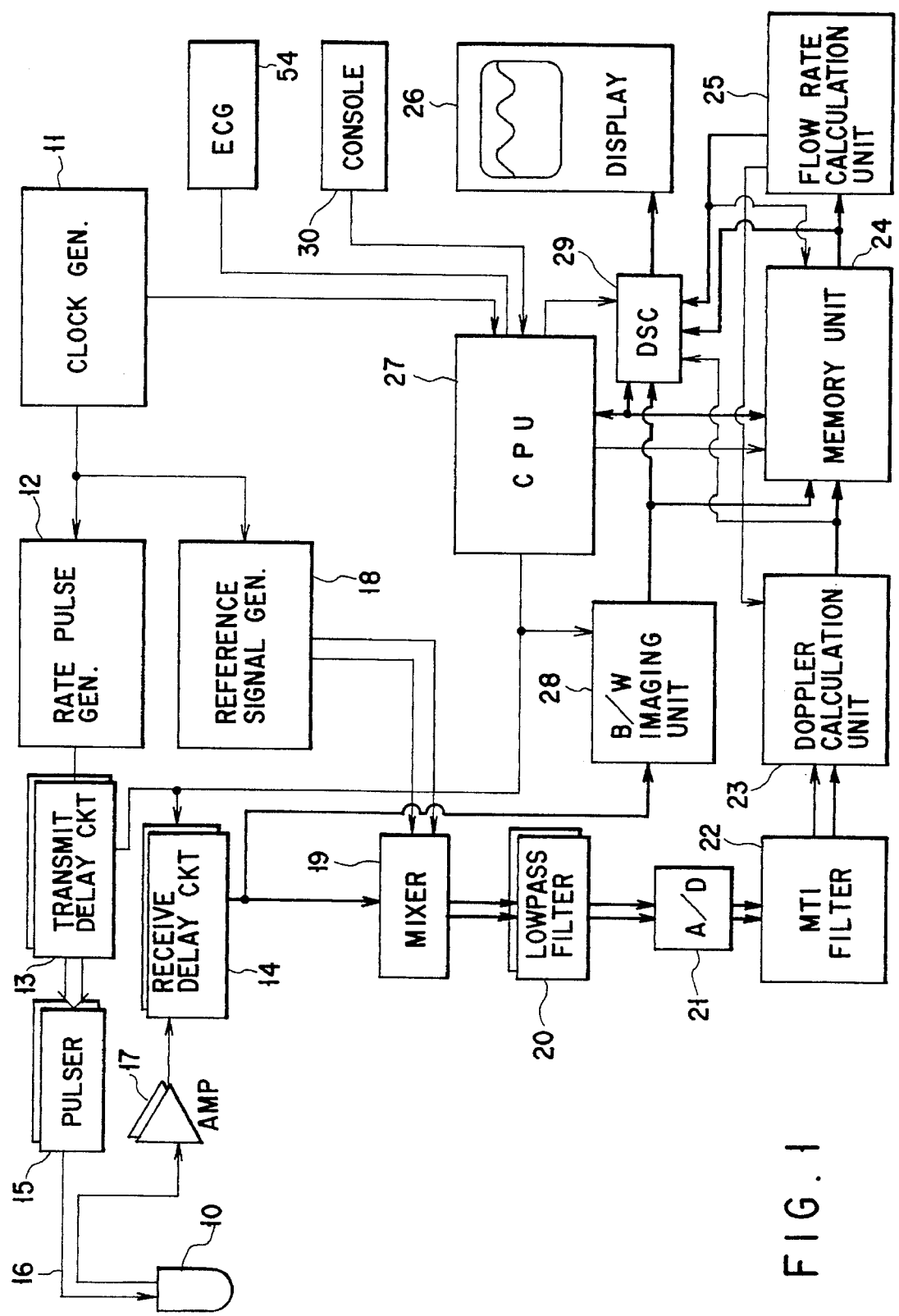
FIG. 1 is a block diagram of an ultrasonic imaging apparatus according to a first embodiment of the present invention.

Referring now to FIG. 1, there is shown an ultrasonic imaging apparatus according to a first embodiment of the present invention, which has a CPU 27 as its center of control and is arranged as follows.

A clock generator 11 generates clock pulses. A rate pulse generator 12 divides the frequency of the clock pulses to generate a rate pulse of a frequency of, say, 5 KHz. The rate pulse is distributed to transmit delay circuits 13 and then fed into pulsers 15. The transmit delay circuits correspond in number to channels and provide to the rate pulse different delay times needed to form an ultrasound beam and steer the beam to a preselected direction. Upon receipt of a rate pulse, each of the pulsers 15 outputs a radio-frequency voltage pulse, which is applied through a cable 16 to a corresponding elementary transducer (corresponding to a channel) of a transducer array attached to the tip of a probe 10. Thus, the probe 10 transmits pulses of ultrasound into a human body under examination. The pulses of ultrasound will reflect at an acoustic impedance boundary. The reflected wave is received by the elementary transducers of the transducer array and the converted into electric signals which, in turn, are fed into receive delay circuits 14 via a cable 16 and amplifiers 17. The receive delay circuits 14 impart channel-dependent delay times to the electric signals, which, in turn, are summed. An output signal of the receive delay circuits 14 is detected by a B/W imaging unit 28. The resulting signal is converted into digital form. Thereby, tomography data is produced which is used to form a B-mode image, i.e., a tissue tomography image. The tomography data is sent to a display 26 via a digital scan converter (DSC) 26 and visually displayed as a tomography image in variable-density form. The tomography data is also sent to a memory unit 24 and stored therein.

The output signal of the receive delay circuits 14 is sent to two mixers 19, where it is multiplied by reference signals of a radio-frequency fundamental frequency fo (for example, fo=3.5 MHz) from a reference signal generator 18, and then applied to two lowpass filters 20. The mixers and lowpass filters construct a quadrature detector circuit, whereby two Doppler signals which are in quadrature and have Doppler-shifted frequency information are obtained. The reference signals applied to the respective mixers are 90-degrees out of phase with each other. Each of the Doppler signals is digitized by a respective one of A/D converters 21 and then sent via MTI (moving-target indicator) filters 22 to a Doppler arithmetic unit 23, where the blood flow velocity is calculated at each of sampling points. Each of the MTI filters 22 is configured as a highpass filter adapted to remove clutter components from reflectors, such as cardiac muscles, which are slow in speed of motion. Only blood-flow-related Doppler signals allowed to pass through the MTI filters 22 are applied to the Doppler arithmetic unit 23. For one scanning line, sampling points are set at intervals of, say, 0.5 mm. The Doppler arithmetic unit 23 calculates the blood flow velocity at each of the sampling points. The blood flow velocity data is sent via the DSC 29 to the display 26 where it is displayed in real time. This technique, which is generally called "color Doppler", has already been put to practical use. If the cutoff frequency of the MTI filters 22 is set at a value equal to or less than the velocity of the cardiac muscle, the motion velocity of the cardiac muscle will be displayed in color. This technique is generally called "tissue Doppler." The flow velocity data from the Doppler arithmetic unit 23 is also sent to the memory unit 24 and stored therein. The flow velocity data is sent from the memory unit 24 to a flow rate calculation unit 25, which calculates blood-flow-related quantities, such as flow rate, single stroke volume, cardiac output, etc., from the flow velocity data.

An electrocardiograph (ECG) 54 provides an electrocardiogram waveform corresponding to motion of the heart as changes in voltage. Its output, i.e., an electrocardiogram waveform, is sent via the CPU 27 and the DSC 29 to the display 26 where it is displayed momentarily below a tomography image. The electrocardiogram data is sent from the CPU 27 to the memory unit 24 for storage.

FIG. 2 is a plan view of the console 30, which is equipped with a switch 101 for turning on or off the flow rate measurement mode, switches 102 to 104 for selecting an angle of view for a scan area in the Doppler mode, a switch 105 for steering a scan area in the Doppler mode, and a memory start switch 106 which is operated when it is desired to store tomography data, flow velocity data, overlay data and electrocardiogram data in the memory unit 24. For reproduction and display of stored tomography data after the termination of the scan, the console 30 is equipped with a switch 107 for instructing the start of reproduction, a switch 108 for instructing the stop of reproduction, a switch 109 for instructing slow reproduction, a switch 110 for instructing freeze (still-frame) reproduction, a switch 111 for instructing fast-forwarding reproduction, and a switch 112 for instructing reverse reproduction. Furthermore, for setting an ROI as a place where the flow rate is to be obtained, the console has a switch 113 for instructing the start of setting of an ROI, a trackball (or a mouse or a digitizer) 114 for tracing the ROI with the cursor on the screen of the display 26, and a subswitch 115. The console is further provided with a switch 116 for instructing the start of flow rate calculation after the ROI has been set.

Figure 3:
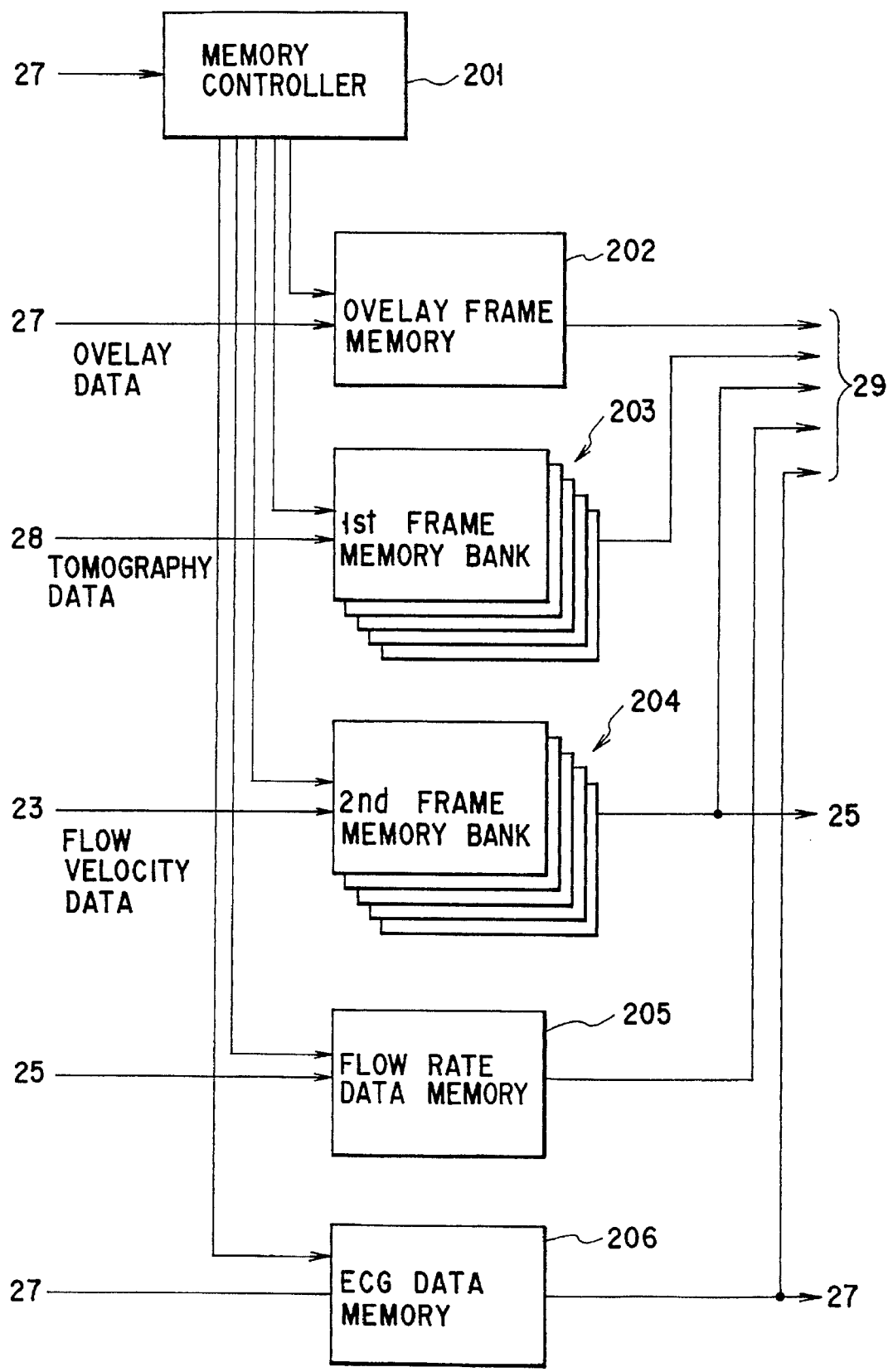
FIG. 3 a diagram of the memory unit of FIG. 1.

FIG. 3 is a block diagram of the memory unit 24, which is constructed from a memory controller 201 serving as a subcontroller of the CPU 27, an overlay frame memory 202 for storing overlay data, a first frame memory bank 203 for storing n frames (n≦1) of tomography image data, a second frame memory bank 204 for storing n frames of blood flow velocity data, a flow rate data memory 205 for storing flow rate data calculated by the flow rate calculation unit 25, and an electrocardiogram data memory 206.

Next, the operation of the present invention will be described. Suppose that a sector scan is used. whereas a B-mode scan area has an angle of view of, for example, 90°, a Doppler-mode scan area has an angle of view selected from among 15°, 20°, 30°, 45°, and 60° by way of example. Since the Doppler mode is narrower in angle of view than the B mode, the Doppler-mode scan area is included in the B-mode scan area. An ultrasound propagation path, which is determined by delay control of transmission/reception of ultrasonic waves, is referred to as a scanning line. The B-mode scan area involves a plurality of scanning lines, while the Doppler-mode scan area includes a smaller number of scanning lines, for example, eight scanning lines. In the B-mode scan, the transmission/reception of ultrasonic waves is performed once for each scanning line within the scan area. In the Doppler-mode scan, on the other hand, the transmission/reception of ultrasonic waves is performed, twice or more times, for example, 16 times for each scanning line within the Doppler-mode scan area. In a one-frame scan, the B-mode scan and the Doppler-mode scan are mixed so that tomography image data and flow rate data will be substantially in time phase. This mixed scan is referred to as a B/D-mode scan. In the B/D-mode scan, transmission/reception of ultrasound is performed once for each of scanning lines which are outside the Doppler-mode scan area but inside the B-mode scan area. For each of eight scanning lines which are included in the Doppler-mode scan area within the B-mode scan area, the B-mode transmission/reception is performed once and then the Doppler-mode transmission/reception is repeated 16 times.

Figure 5A:
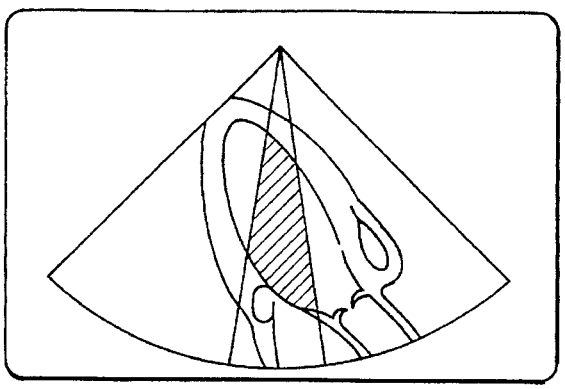
FIGS. 5A and 5B show display images before and after the start of blood flow measurement mode.
Figure 5B:
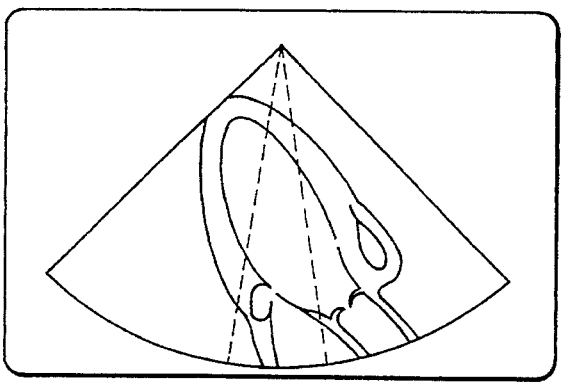

FIG. 4 is a timing diagram illustrating an operating procedure by an operator required for measurement of the flow rate in the present embodiment. To measure the flow rate, a B/D-mode scan is carried out. At first, the switch 101 is in the OFF state. In this state, a color image of blood flow velocity is displayed superimposed on a tomography image in real time on the display 26 as shown in FIG. 5A, which remains unchanged from the conventional technique. When the switch 101 is moved to the ON position, the flow rate measurement mode is started. In this mode, the CPU 27 displays a color image of blood flow velocity or creates overlay data indicating a Doppler-mode scan area on the screen. This overlay data is frame data. The Doppler-mode scan area is defined by dotted-line markers that surround it. After the flow rate measurement mode has been started, as shown in FIG. 5B, the display 26 displays the color image of blood flow velocity shown in FIG. 5A, or the color display of blood flow velocity disappears and the dotted-line markers defining the Doppler-mode scan area is displayed superimposed on the tomography image in real time.

In this state, while watching the tomography image the operator first operates the probe 10 to fit its scanning plane to an optimum sectional plane which is here a longitudinal section of the heart that passes through the center of the cross section of the blood outflow tract of the left-ventricle. That is, the operator adjusts the probe's location and angle of contact with respect to the chest of the human body under examination. For diagnosis of diseases of the circulatory system whose typical organ is the heart, the selection of an optimum sectional plane is essential for measurement of the flow rate with high accuracy. The blood flow can be observed in real time when the image of blood flow velocity (FIG. 5A) is displayed. The flow velocity image disappears and only the dotted-line markers and the tomography image are displayed. This display format will eliminate the drawback that the flow velocity image can hardly be observed, and will make it possible to fit the scanning plane to the optimum plane.

Figure 6A:
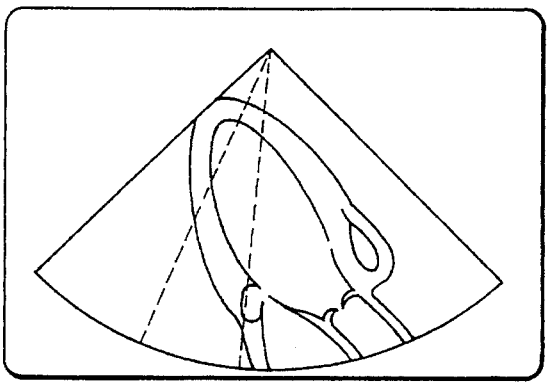
FIGS. 6A and 6B are diagrams for use in explanation of steering.
Figure 6B:
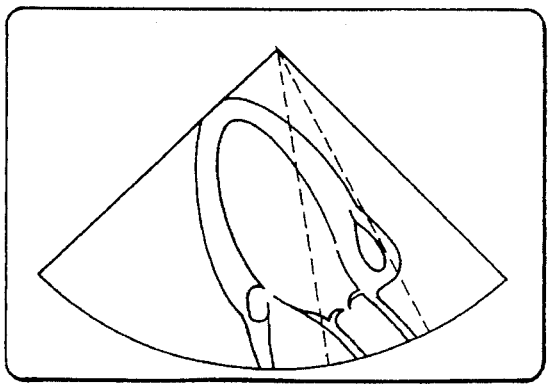
Figure 7A:
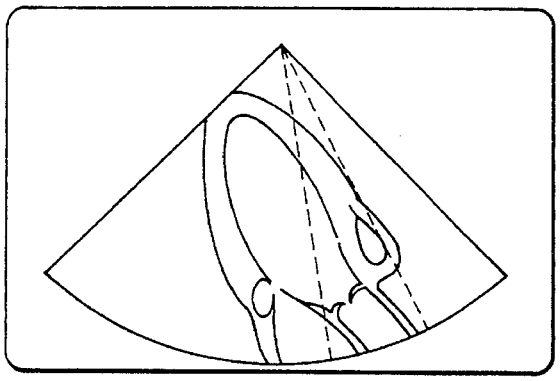
FIGS. 7A and 7B are diagrams for use in explanation of angle of view.
Figure 7B:
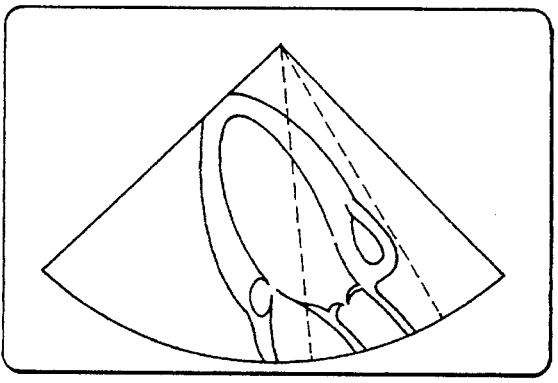

After the scanning plane has been matched with the optimum plane, with the location and angle of the probe 10 held, the operator operates the switch 105 while watching the marker to steer the Doppler-mode scan area as shown in FIGS. 6A and 6B so that the Doppler-mode scan area will cover the cross section of the left ventricle blood outflow tract to a minimum, and operates the switches 102 to 104 to select among angles of view of the Doppler-mode scan area as shown in FIGS. 7A and 7B.

Figure 8A:
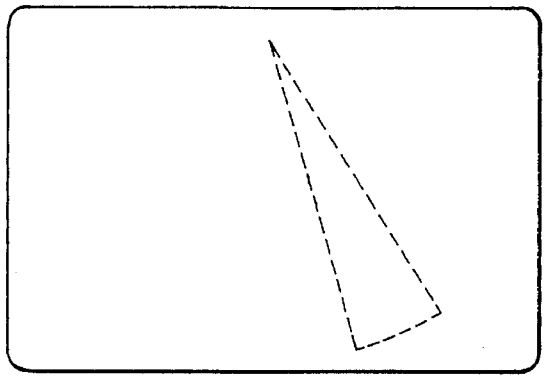
FIG. 8A shows an example of an overlay image stored in the overlay memory of FIG. 3.
Figure 8B:
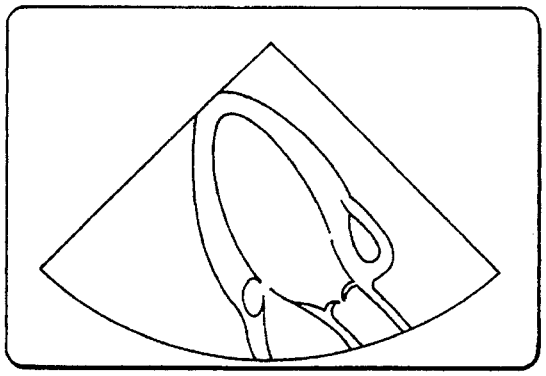
FIG. 8B shows an example of a B-mode image stored in the first frame memory bank of FIG. 3.
Figure 8C:
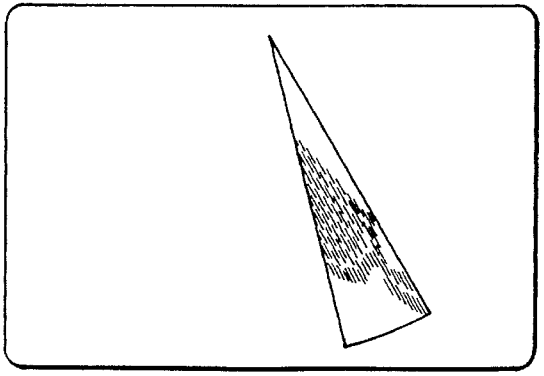
FIG. 8 shows an example of a blood flow image stored in the second frame memory bank.

Next, the operator operates the memory start switch 106. Consequently, overlay data at this point of time (refer to FIG. 8A) is sent from the CPU 27 to the overlay frame memory 202 and stored therein. After the operation of the switch 106, n frames of tomography data (refer to FIG. 8B) corresponding to multiple heart-beat cycles (for example, five to ten cycles of the heart beat) are stored in the first frame memory bank 203. To each frame of tomography data is attached as attribute information about the timing of data acquisition that corresponds to the elapsed time from the memory start. Moreover, n frames of flow velocity data (refer to FIG. 8C) corresponding to multiple heart beat cycles (for example, five to ten cycles) after the operation of the switch 106 are stored in the second frame memory bank 204. Likewise, information about the timing of data acquisition corresponding to the elapsed time from the memory start is attached to each frame of flow velocity data as an attribute. Furthermore, electrocardiogram data for multiple heart beat cycles after the operation of the switch 106 are stored in the data memory 206. Likewise, information about the timing of data acquisition is attached to the electrocardiogram data as the elapsed time from the memory start.

The tomography data, the flow velocity data and the electrocardiogram data, for which the timing of data acquisition is known, can be displayed in a sequential order of time. It is also possible to establish a time correspondence among these types of data.

The memory unit 24 may be arranged to constantly store a fixed amount of data, for example, ten seconds of data, in such a way as to cause data stored more than ten seconds previously to overflow, and when memory stop is instructed, store ten seconds of data immediately before that instruction.

Upon completion of the storage of tomography data, flow velocity data and electrocardiogram data for a predetermined number of heart beat cycles, the B/D mode scan is automatically terminated under the control of the CPU 27.

After the termination of that scan, the operator operates the reproduction start switch 107 at an arbitrary point of time. Thereby, the tomography data are read from the first frame memory bank 203 of the memory unit 24 in sequence at the same frame rate as that at the time of data acquisition and sent via the DSC 29 to the display 26, thus permitting the tomography images to be visually displayed as moving pictures. Displaying tomography data stored in the memory unit 24 as moving pictures after the termination of scan (as opposed to displaying images in real time during scan operations) is defined herein as "reproduction". The color image of flow velocity or the overlay data is read from the overlay frame memory 202 of the memory unit 24 and then displayed superimposed on the tomography images on the display 26 as a marker representing a Doppler-mode scan area.

The frame rate at which and the sequence in which the tomography data are read from the memory unit 24 can be changed. Suitable operating of the switches 109 to 111 allows tomography images to be reproduced at any speed, a specific tomography image to be displayed in a freeze-frame manner, and the images to be reproduced in the reverse direction. It is preferable that, after n frames of tomography data stored in the memory unit 24 have been reproduced, they should be displayed again from the beginning under the control of the CPU 27, that is, they should be reproduced endlessly.

Figure 9:
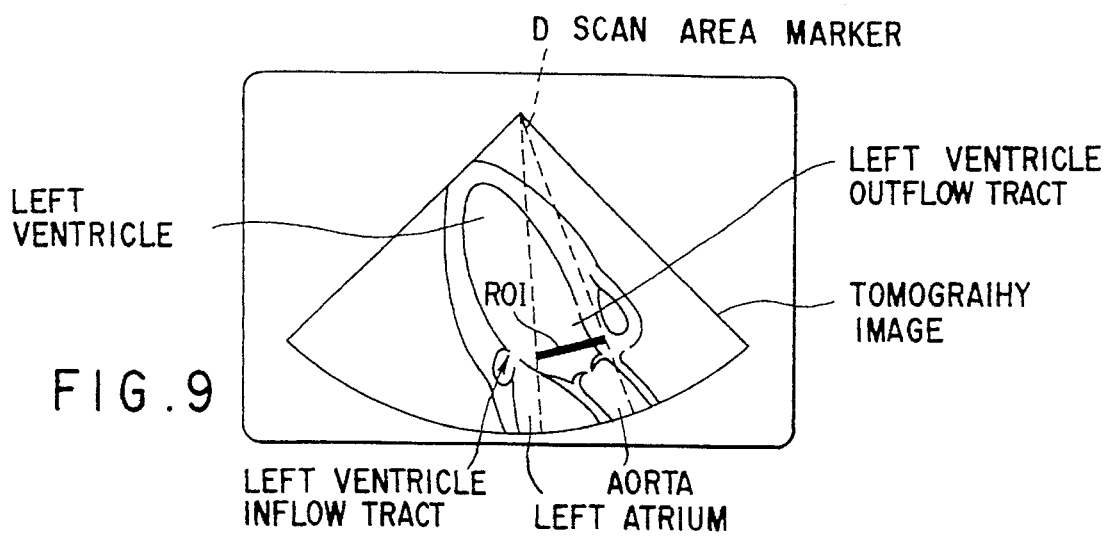
FIG. 9 shows an example of a display image when an ROI is set.

Next, the operator operates the switch 113 to set up an ROI. By this operation, a cursor is displayed superimposed on the tomography image on the display 26. The operator operates the trackball 114 to trace an ROI in an optimum position on the displayed tomography image. FIG. 9 illustrates a state in which an ROI has been set up.

After the ROI has been set up, the operator operates the switch 116 to instruct the CPU to start calculations of flow rate. The ROI position information is sent from the CPU 27 to the memory controller 201, which, in turn, controls the second frame memory bank 204 to allow velocity data at sampling points associated with the ROI to be read out to the flow rate calculation unit 25. The flow rate calculation unit 25 calculates the flow rate from the velocity data from the memory bank 24. The volume data is sent via the DSC 29 to the display 26, so that it is displayed in the form of numeric representation or in the form of a graph indicating changes of the flow rate with respect to time, or in both the forms. The graph data may be created in the DSC 29, for example. The flow rate data is sent to the volume data memory 205 and stored therein together with information on data acquisition times.

As described above, for diagnosis of circulatory system diseases, the proper setup of a sectional plane and an ROI is essential for high-accuracy measurements of the flow rate. The present embodiment allows the operator to select an optimum cross section by using the probe 10 while watching tomography images. The sectional plane must be set up with great care, particularly when the blood stream volume is measured simultaneously at the outflow tract and the inflow tract. After the termination of the scan, the operator is allowed to set up an ROI while watching reproduced tomography images. That is, the ROI setting operation need not be performed concurrently with the scan. Thus, the operator can dedicate himself or herself to the operation of the probe during scanning for the purpose of selecting an optimum cross section. Further, after termination of the scan, the operator is allowed to dedicate himself or herself to the operation of setting an ROI. Therefore, an environment is provided which enables a cross section to be selected and an ROI to be set up in a more efficient manner. Thereby, the flow rate will be measured with high accuracy.

Figure 10A:
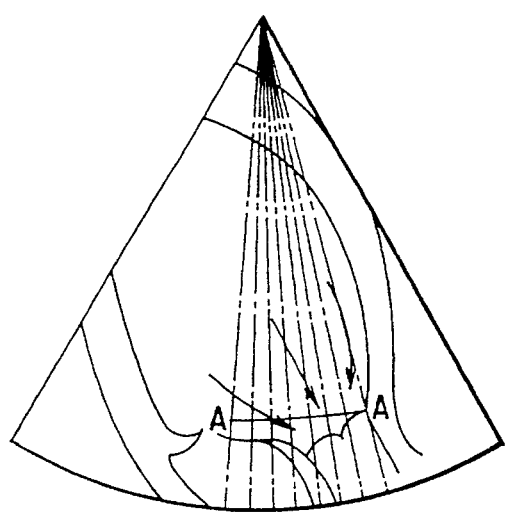
FIGS. 10A, 10B and 10C are diagrams for use in explanation of the way the ROI is set.
Figure 10B:
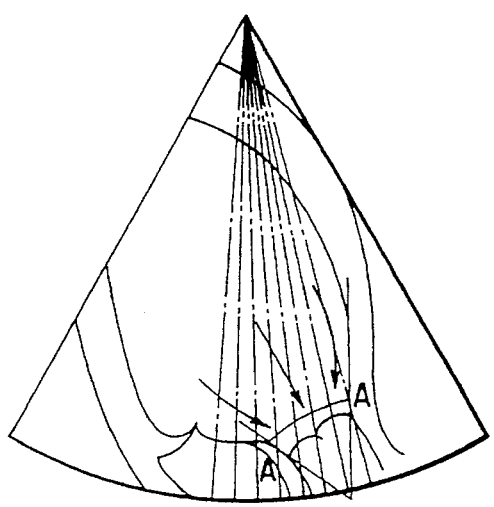
Figure 10C:
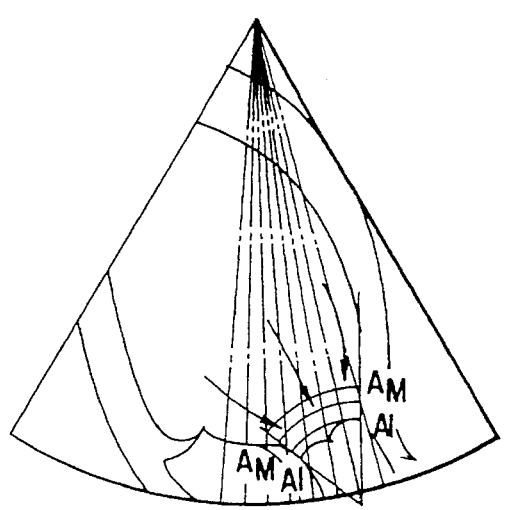

Next, the way an ROI is set up will be described. Suppose here that the present embodiment is applied to the case where outflow volume is obtained. The cross section of the left-ventricle outflow tract is substantially circular. In this case, the optimum section is that longitudinal section of the heart which passes through the center of the cross section of the left-ventricle outflow tract. The position of the optimum ROI is a place where it crosses the left-ventricle outflow tract. To obtain the flow rate, the orthogonal-to-beam method and the orthogonal-to-flow method have been proposed. The method used in the present embodiment is not limited to one of them. FIG. 10A illustrates an ROI according to the orthogonal-to-beam method, FIG. 10B illustrates an ROI based on the orthogonal-to-flow method, and FIG. 10C shows an ROI based on an advanced orthogonal-to-flow method. In FIGS. 10A, 10B and 10C, each of scanning lines in the Doppler mode is indicated by a dashed-and-dotted line, and each of blood flow vectors is indicated by an arrow.

Figure 11A:
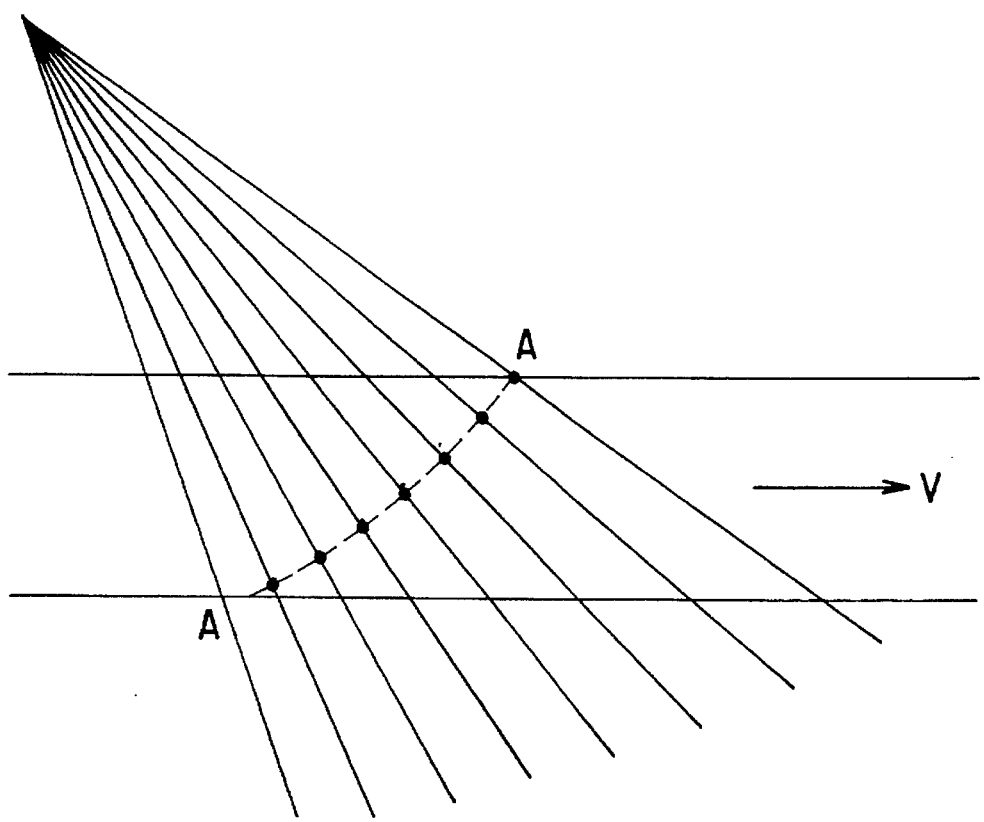
FIGS. 11A and 11B are diagrams for use in explanation of two typical blood flow measurement methods.
Figure 11B:
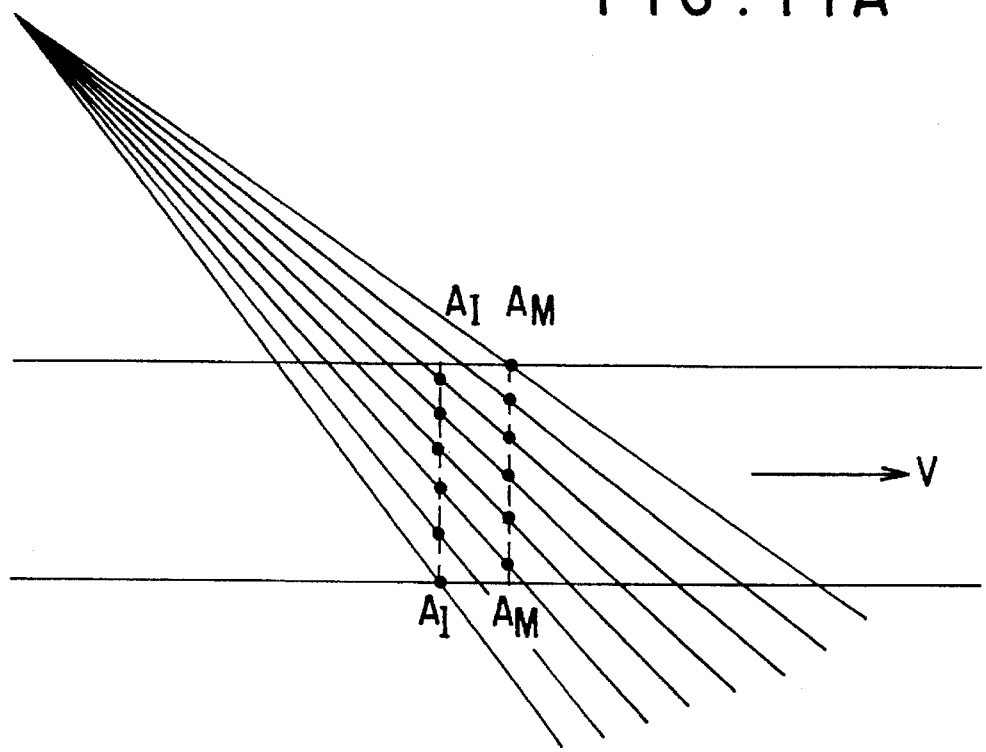

With the orthogonal-to-beam method, the ROI A—A is traced by a straight line, a curved line, or a mixed line such that it crosses the left-ventricle outflow tract and is orthogonal to all the scanning lines in the Doppler mode. With the orthogonal-to-flow method, the ROI A—A is traced by a straight line, a curved line or a mixed line such that it crosses the left-ventricle outflow tract and is orthogonal to blood flow vectors. In order to obtain the absolute blood flow velocity, it is required to obtain an angle between each trace and the flow direction. With the orthogonal-to-beam method, the operator simply traces an ROI in such a way as to link points on the eight scanning lines which are located at the same depth. Since the ROI setting is easily made automatic, the operator simply adjusts the depth. Thus, the orthogonal-to-beam method has an advantage that the ROI setting operation is simple, but, at the same time, it has a disadvantage that it requires troublesome work to input an angle for each scanning line. With the orthogonal-to-flow method, the operator is required to recognize the flow velocity vectors and set an ROI so that it intersects each of the vectors at right angles. It is troublesome, but there is no need of inputting angles. As shown in FIG. 10C, a plurality of concentric ROIs may be set up. In this case, the measurement accuracy will increase with an increasing number of sampling points in comparison with a single ROI. Since the probe acquires data at a time and the ROI is set up at another time, a single ROI or a plurality of ROIs can be set up for the same data. This helps to increase the measurement accuracy. Furthermore, ROIs can be set up for both the inflow tract and the outflow tract with regard to the same data. It is almost to impossible to set up ROIs at the same time the sectional plane is set. To measure the flow rate in a blood vessel with the orthogonal-to-beam method, an ROI is set as shown in FIG. 11A. With the orthogonal-to-flow method, on the other hand, an ROI is set as shown in FIG. 11B.

Next, the flow rate measurement will be described. Generally it is considered that the cross section of blood vessels (artery system) and the left-ventricle outflow tract are circular and the flow velocity distribution is symmetrical with respect to the axis. The cross section of a blood vessel is considered as a collection of concentric annulus rings. Each of the annulus rings is set such that a single sampling point is present in the center of its width. Suppose that the spacing between adjacent sampling points is a. The width of each annulus ring is a. Considering that a sampling point is present in the center of the cross section of the blood vessel, the distances between the center and the respective sampling points are a, 2a, 3a, etc. The inside radii of the respective annulus rings are a/2, a+a/2, 2a+a/2, etc. Suppose here that the inside radius of the i-th annulus ring from the center is Ri. Then, the cross-sectional area Si of the i-th annulus ring will be given by $$S_i = \pi \cdot Ri^2 - \pi \cdot Ri - 1^2$$
$$= \pi \cdot (Ri^2 - Ri - 1^2)$$

Suppose that the absolute flow velocities at the respective sampling points are v1, V2, ..., Vi, ..., Vn. Supposing that the flow velocity distribution is symmetrical with respect to the cross-sectional center of the blood vessel, the flow rate qi flowing through the i-th annulus ring will be given by $$qi = Vi \times Si$$

Thus, the flow rate Q flowing through the entire blood vessel is given by $$Q = \sum_{i=1}^{n} qi$$

The flow velocity distribution is not always perfectly symmetrical; thus, it is normal to use the average of flow velocities at two sampling points equidistant from the center of the blood vessel as Si.

Figures 12A, 12B:
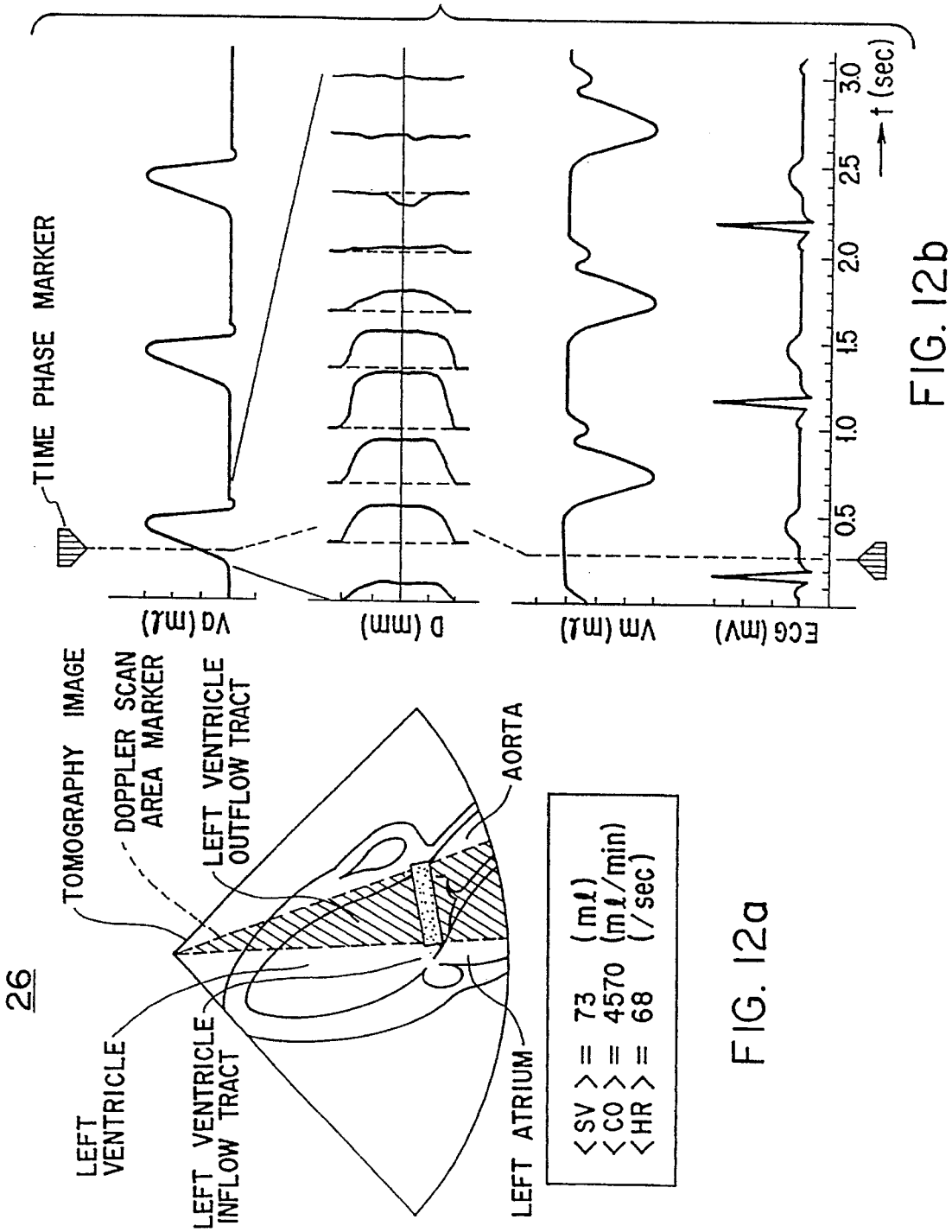
FIGS. 12A and 12B together show an example of a display image.

Next, the display method for the display 26 will be described. FIGS. 12A and 12B together show an example of a display image on the display 26. The display image described herein is implemented under the control of the CPU 27. If scan is made at a frame period of 64 ms, then about 16 frames of tomography data and velocity data will be obtained each second. For example, five seconds of data are stored in the memory unit 24 together with electrocardiogram data. With about 16 frames per second, 80 frames of two-dimensional data will be stored during five seconds. Since each piece of data has timing information, flow rate data obtained by the flow rate calculation unit 25 will also have the timing information. Thus, the tomography image frames can be associated with the electrocardiogram waveforms.

Figures 13, 14:
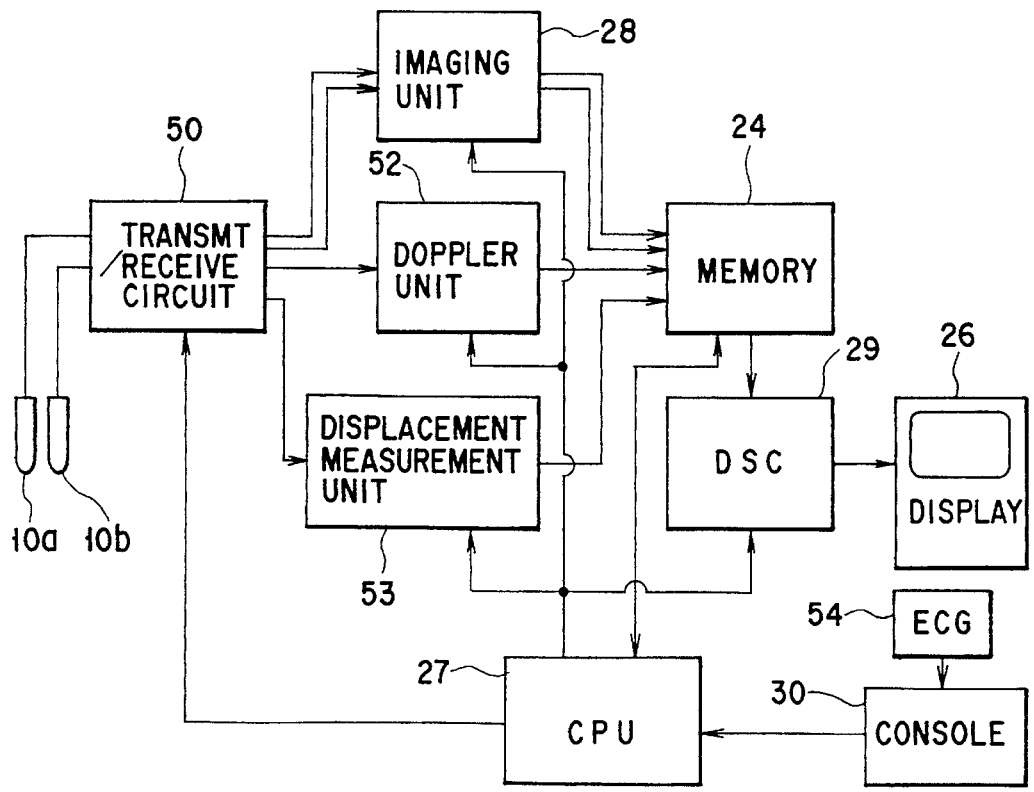
FIG. 13 is a correspondence table for various items of data.
FIG. 14 shows, in block diagram form, a modification of the ultrasonic imaging apparatus of FIG. 1.

FIG. 13 is a table of tomography image frames numbered according to the time sequence in which they are obtained and the corresponding electrocardiogram voltages, left-ventricle outflow volumes, left-ventricle inflow volumes, etc. This table is created in the CPU 27 and stored in its internal memory or the memory unit 24. In addition, to obtain flow velocity profiles, flow velocity data at each sampling point is added as needed. The CPU 27 creates various graphs, which will be described later, on the basis of the flow velocity data and the flow volume data. These items of graph data are displayed, as shown in FIG. 12B, as various time-varying waveforms on the screen of the display 26 on which a tomography image is displayed simultaneously. The graph data may be created either by the CPU 27 or by the volume flow rate calculation unit 25.

As shown in FIGS. 12A and 12B, the tomography image and the marker indicating a Doppler-mode scan area are displayed at the left of the screen of the display 26 and various items of data are displayed at the right of the display screen in graphic form with abscissa taken as time axis. Under the tomography image the single stroke volume (SV), the cardiac output (CO) and the average heart rate (HR) are numerically displayed like "SV=73(ml)", "CO=4570(ml/min)" and "HR=68 (/sec)".

At the top of FIG. 12B there is shown a graph which represents changes of the flow rate from the left-ventricle outflow tract in which the ROI has been set up with respect to time. Below the flow rate graph are shown velocity profiles obtained at regular intervals of time, each of which indicates the flow rate distribution as a function of position D in the direction of diameter of the left-ventricle outflow tract. From changes of these velocity profiles with respect to time it will be observed that the flow velocity distribution in the direction of diameter of the left-ventricle outflow tract changes momentarily. Below the velocity profile graph is shown a graph representing changes of the inflow volume from the left-ventricle inflow tract in which the ROI has been traced with respect to time. Although the outflow volume and the inflow volume are not in time phase, they are equal to each other in the average of flow rate per heart stroke. At the bottom of FIG. 12B is shown a graph representing an electrocardiogram waveform.

In order to measure the outflow and the inflow volume at the same time, it is required to set a Doppler-mode scan area wide enough to cover both the left-ventricle outflow and inflow tracts. It is further required to set up two ROIs, one for the left-ventricle outflow tract and one for the inflow tract, and to obtain the flow rate for each ROI. Instead of providing two ROIs, a single ROI may be provided which is long enough to extend from the outflow tract to the inflow tract. In this case, the outflow volume will be obtained from the blood flow velocity of positive polarity and the inflow volume will be obtained from the blood flow velocity of negative polarity.

All the graphs are displayed in time phase coincidence. The CPU 27 allows the position of a time-phase marker which is placed along the time axis of the graphs of FIG. 12B to correspond with the time phase of the tomography image of FIG. 12A. For example, when tomography images are reproduced in moving-picture mode, in fast-forward mode, or in reverse mode, the time-phase marker will move right and left correspondingly, permitting the relationship between each tomography image and numeric values on the graphs to be indicated clearly to the operator. When the operator uses the trackball 114 to move the time-phase marker, the CPU 27 permits a tomography image corresponding in time phase to the time-phase marker to be displayed. On the second graph from the top as well, the corresponding time phase is indicated by a broken line.

The electrocardiogram data must be displayed at intervals of a time shorter than the frame interval. As will be described later, the time interval between frames of FIG. 13 can be divided into shorter intervals to use interpolated data for data other than electrocardiogram data.

The multiplication of the single stroke volume and the average heart rate results in the cardiac output, which is expressed in ml/min and displayed below the tomography image together with the average heart rate.

Of these items of data, only necessary data can be selectively recorded by the use of a dedicated keyboard, or a conventional keyboard or mouse. In addition, it is easy to add observations as needed.

As described above, by temporarily storing multiple frames of tomography data and velocity data in the memory unit 24, the operator can to perform an operation of selecting a sectional plane and an operation of setting an ROI separately. That is, the operator can to devote himself to the operation of the probe 10 during scan and to the operation of setting an ROI after termination of the scan without being worried about the operation of the probe. This means that the operator can afford to fit the scanning plane to the optimum plane section of a body and to set the ROI in the optimum position. This will provide highly accurate measurements of the flow rate.

The use of such a system in which the sectional plane selecting operation and the ROI setting operation are performed at different times permits data required to diagnose other diseases of circulatory organs to be obtained simultaneously with the flow rate measurement. Hereinafter, a description will be made of a modification of the first embodiment which permits such data to be obtained simultaneously.

Normally a single probe is used. If changes in the diameter of a blood vessel (for example, aorta) that is proportional to blood pressure and the flow rate are measured simultaneously, then indications (for example, pressure, capacity pressure, etc.) that are useful in evaluating the function of the circulatory system (the heart in particular) will be obtained. FIG. 14 is a simplified block diagram of an ultrasonic imaging diagnosis apparatus employing two probes 10a and 10b. Note that the rate pulse generator 12, the transmit delay circuits 13, the pulser 15, the amplifiers 17 and the receive delay circuits 14 of FIG. 1 are included in a transmitter/receiver circuit 50. Likewise, the mixer 19, the lowpass filters 20, the reference signal generator 18, the A/D converter 21, the MTI filter 22 and the Doppler calculation unit 23 are included in a Doppler unit 52. The components corresponding to those in FIG. 1 are denoted by like reference numerals.

The outputs of imaging unit 28 and Doppler unit 52 are input to the memory unit 24 and then fed into the DSC 29 for display on the display unit 26. Measured data on changes in the diameter of a blood vessel obtained by a displacement measurement unit 53 is sent to and stored in the memory unit 24 together with a cross-sectional image of that vessel captured by the same transducer. The timing of acquisition of an electrocardiogram waveform or an R wave obtained by the electrodcardiograph 54 is stored in the memory unit 24 via the console 30 and the CPU 27. When the doctor selects a suitable sectional plane to measure the flow rate and changes in vessel diameter by means of the respective probes 10a and 10b and then presses the memory start button 106 on the console 30, measured data for several heart beats (for example, five to ten heart beats) are stored in the memory unit 24 as in the flow rate measurement. Subsequent operations permit the CPU 27 to calculate desired indications used to evaluate the function of the heart and display them in graphic form or in numerical representation on the display 26. In this case, the operator can enter the patient's maximum and minimum blood pressures already measured via the console 30 to calculate parameters associated with the function of the heart.

In the diagnosis of diseases of circulatory organs whose typical organs are blood vessels and the heart, the selection of an optimum sectional plane for measurement is essential for acquisition of highly accurate, reproducible data. In the present embodiment, the doctor is allowed to devote himself to the selection of an optimum sectional plane and, after data obtained for that plane is stored temporarily, to set an ROI in the most suitable position for flow rate measurement, which permits highly accurate, reproducible flow rate data to be obtained readily. Thus, the measurement of quantitative parameters associated with the function of the heart using ultrasonic waves becomes practical. Further, for the measurement of flow rate (cardiac output in particular) using ultrasonic beams in multiple directions, either one or both of the orthogonal-to-beam method and the orthogonal-to-flow method can be used. In addition, multiple curved lines or a plurality of areas, such as the left outflow tract and the left outflow tract, can be set, making it possible to provide an increased number of items of data for raising the measurement accuracy. In particular, the orthogonal-to-flow method which can sufficiently cover the left-ventricle outflow tract but has somewhat complicated operability provides a significant improvement in operability, thus permitting highly accurate measurement to be put to practical use. Although each of the scanning lines has a time delay, stored data for multiple heart beats can be used to perform calculations such that time differential errors are minimized by means of interpolation. In addition, many types of data, such as flow rate, electrocardiogram, changes in vessel diameter, maximum and minimum blood pressure, etc., can be entered to calculate heart-function parameters associated with these values, expanding the capabilities significantly.

Moreover, tomography images and time-varying graph data such as flow rate can be displayed on the same screen in time-phase coincidence, which permits the function of the heart to be analyzed in detail at each time phase. By so doing, only necessary information can be recorded surely and attached information can also be added; thus a recording of optimum medical data is permitted.

As the heart beats, the inflow tract and the outflow tract change their positions momentarily. In this case, the annular part of the aorta or vulva mitralis may be automatically detected by means of outline extraction, and the ROI already set may be moved in accordance with the position of the outline part detected, so that the ROI may follow the moving outflow or inflow tract.

Now, the features according to a second embodiment will be described. A scan is defined as an operation of acquiring one frame of data. This scan is a sequential scan in which a sequential series of scanning lines is moved across a scan area. Thus, there is some time delay between each scanning line and the next adjacent scanning line. This time delay is significant in the Doppler mode in which transmission/reception of ultrasonic waves is repeated a number of times, for example, 16 times for each scanning line. The present embodiment substantially eliminates the time delay between scanning lines by substantially unifying the time of data acquisition at each of sampling points within a scan area to a specific time. To eliminate the time delay problem associated with scanning lines, the present embodiment creates data that is not actually acquired at the unified time by interpolating two items of data which are backward and forward in time.

Figure 15:
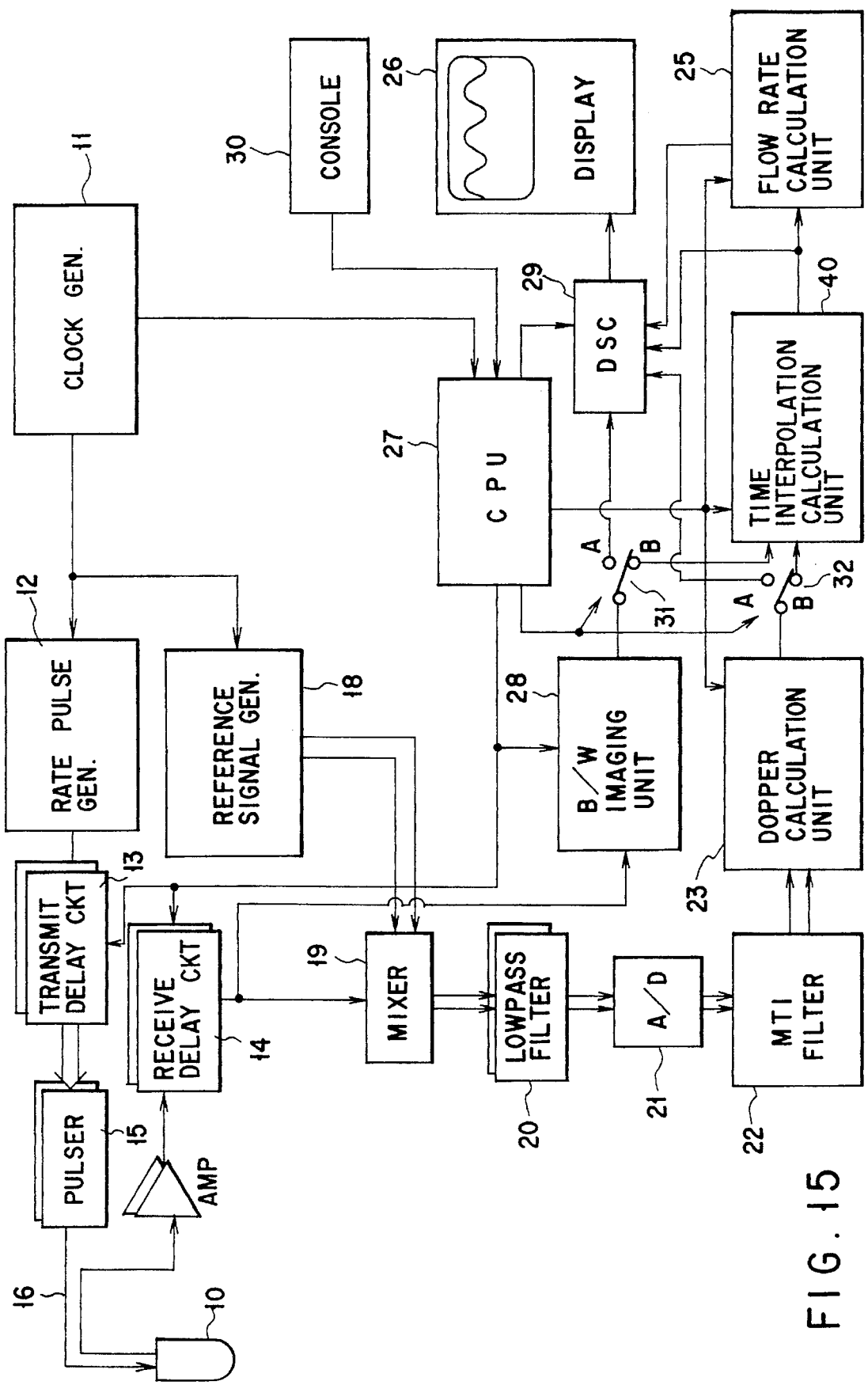
FIG. 15 is a block diagram of an ultrasonic imaging apparatus according to a second embodiment of the present invention.

FIG. 15 shows, in block diagram form, an ultrasonic diagnosis apparatus according to the second embodiment of the present invention. The corresponding parts to those in FIG. 1 are denoted by like reference numerals and descriptions thereof are omitted. The output of the B/W imaging unit 28 is selectively connected by a switch 31 to either the DSC 29 or the time interpolation calculation unit 40. When the switch 31 is set to the position A, the DSC 29 is directly connected to the imaging unit 28. When the switch is set to the position B, on the other hand, the DSC is connected to the imaging unit 28 through the time interpolation unit 40.

Either of the DSC 29 and the time interpolation calculation unit 40 is selectively connected by a switch 32 to the Doppler calculation unit 23. When the switch 32 is set to the position A, the DSC is directly connected to the Doppler calculation unit. When the switch 32 is set to the position B, on the other hand, the DSC is connected to the Doppler calculation unit 23 through the time interpolation calculation unit 40.

The switches 31 and 32 are operated simultaneously under the control of the CPU 27. That is, when the terminal A of the switch 31 is selected, the terminal A is selected in the switch 32 as well. The same is true of the terminal B.

When the switches 31 and 32 are each set to the terminal A, tomography image data and velocity data are sent via the DSC 29 to the display 26, where they are visually displayed in real time as moving pictures. When the switches are each set to the position B, on the other hand, tomography data and velocity data from which the time difference between scanning lines has been eliminated by the time interpolation calculation unit 40 are sent via the DSC 29 to the display 26 where they are visually displayed as moving pictures.

The flow rate calculation unit 25 is connected to the output of the time interpolation calculation unit 40 to calculate blood-flow-related quantitative information, such as flow rate, from the velocity data free of time differences. The resulting flow rate data is sent via the DSC 29 to the display 26 where it is displayed in numeric representation or in the form of a time-varying waveform graph.

Figure 16:
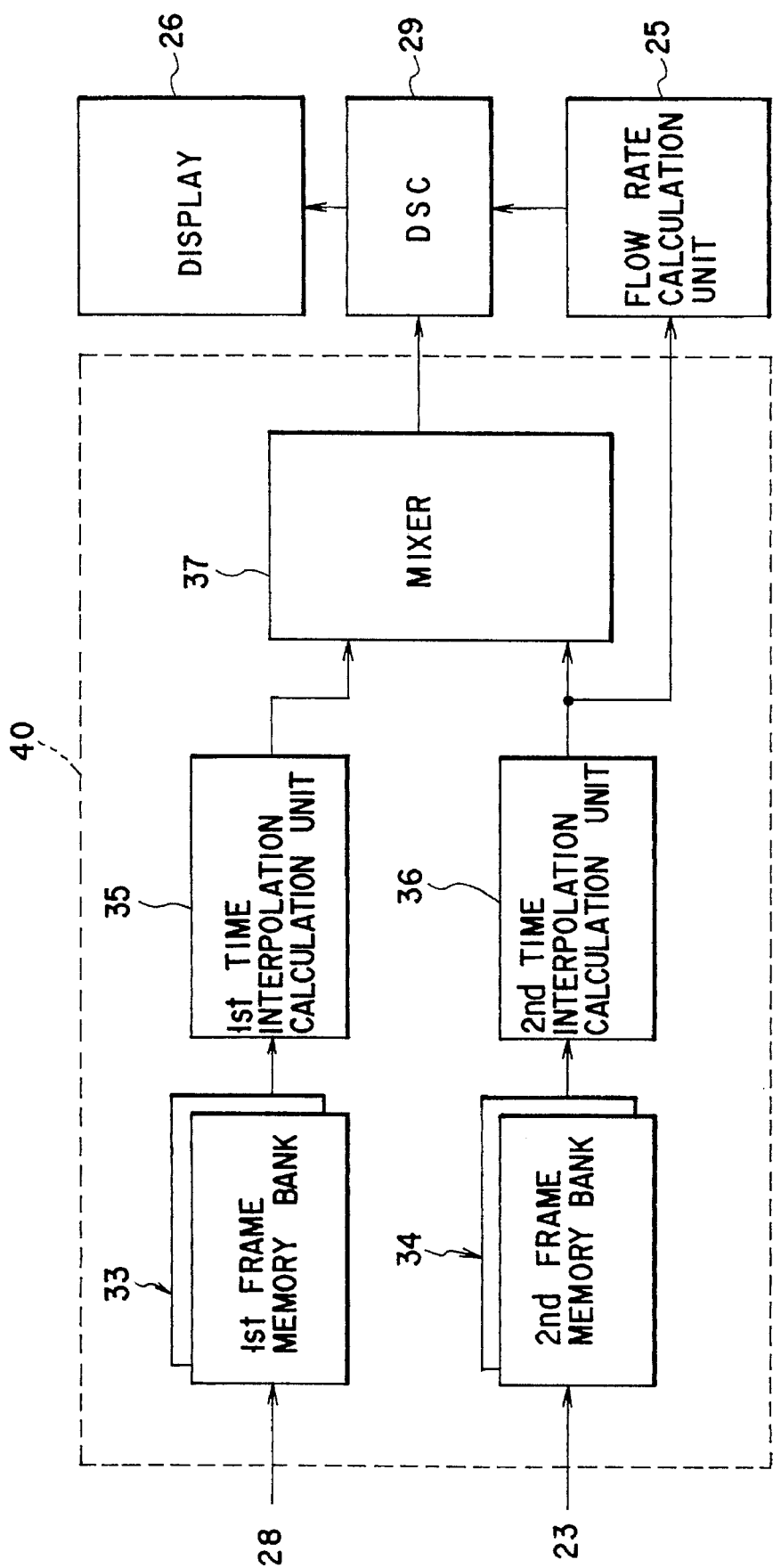
FIG. 16 is a block diagram of the time interpolation arithmetic unit of FIG. 15.

FIG. 16 is a block diagram of the time interpolation calculation unit 40, which includes a first frame memory bank 33 for storing tomography data corresponding to at least two latest ones of successively acquired frames, and a second frame memory bank 34 for storing Doppler data (e.g., blood flow velocity data, power Doppler data or, tissue Doppler data) corresponding to at least two latest ones of successively acquired frames.

The first frame memory bank 33 has its output connected to a first time interpolation calculation unit 35. Likewise, the second frame memory bank 34 has its output connected to a second time interpolation calculation unit 36. The first and second time interpolation calculation circuits 35 and 36 have their outputs connected together to a mixer 37, which is in turn connected to the DSC 29. The second time interpolation calculation unit 36 is connected to the flow rate calculation unit 25.

The first time interpolation calculation unit 35 interpolates two items of tomography data in the first frame memory bank 33 which are backward and forward in time with respect to the same sampling point to produce interpolated tomography data corresponding to that unified time described previously.

The second time interpolation calculation unit 36 interpolates two items of velocity data in the second frame memory bank 34 which are backward and forward in time with respect to the same sampling point to produce interpolated velocity data corresponding to that unified time.

The mixer 37 mixes the tomography image data and the velocity data or the tissue Doppler data which are free of time differences between scanning lines for subsequent application to the DSC 29, so that the tomography image represented in variable density and the velocity image represented in color are displayed superimposed.

Next, the time compensation in the present embodiment will be described. Normally, a B-mode scan for tomography and a Doppler-mode scan for acquiring Doppler data (e.g., velocity data) are mixed in one frame of scan. For convenience of description, however, suppose that one frame of scan comprises a Doppler-mode scan alone. Note that the B-mode is the same as the Doppler-mode for the time compensation processing. Here, suppose that measurement is made of the flow rate discharged from the left ventricle to the whole body through the aorta when the heart muscle contracts, i.e., the cardiac output. Suppose that the rate frequency is 5 KHz and the pulse interval is 200 μs. Suppose further that the transmission/reception of ultrasonic waves is repeated 16 times for each scanning line. It is further supposed that a Doppler-mode scan area is constructed from eight scanning lines. The eight scanning lines are named the 1st scanning line, 2nd scanning line, . . . , and 8th scanning line in the order of scan.

Figure 17:
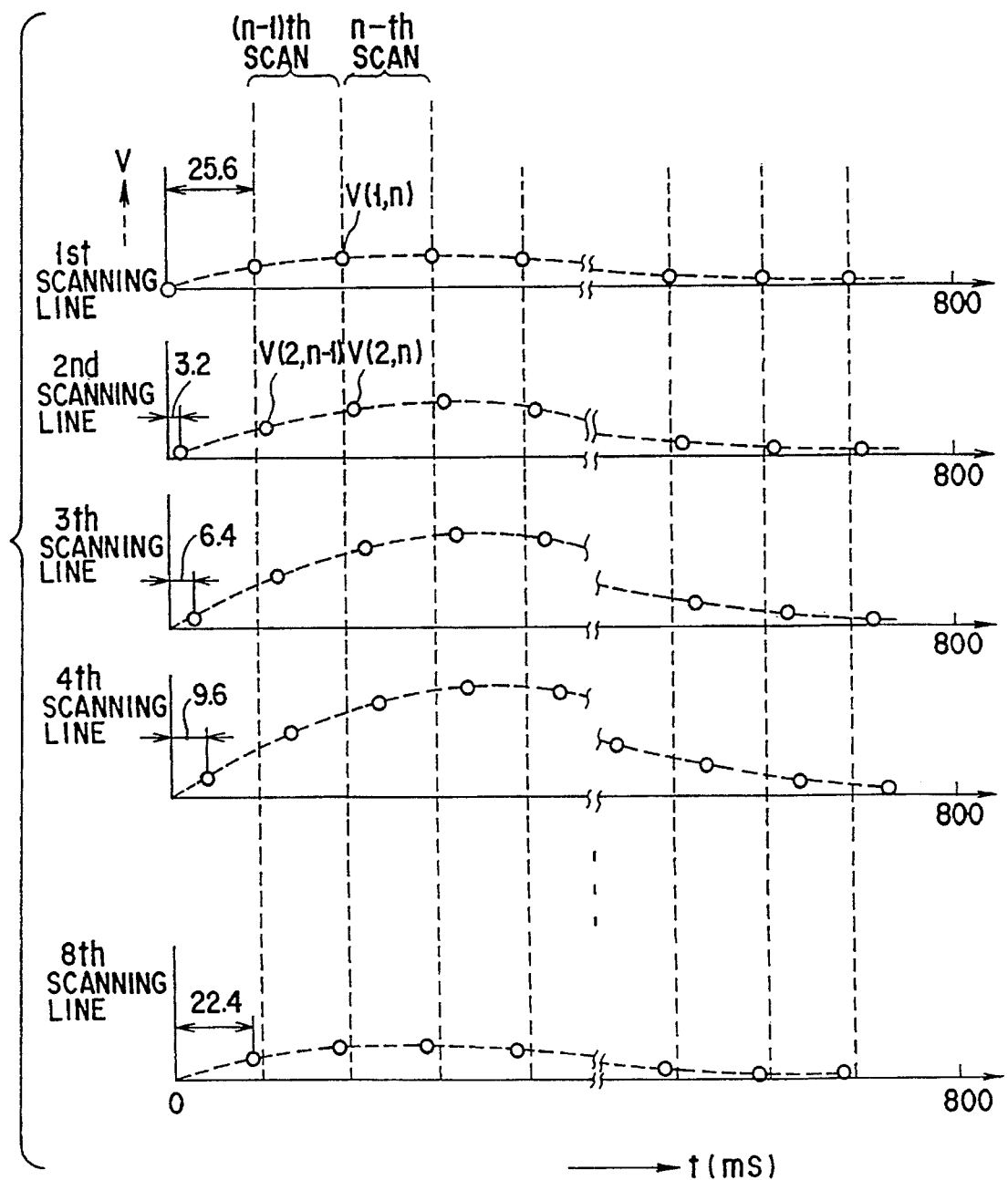
FIG. 17 shows changes in measured value of blood flow velocity with respect to time for each scanning line.

FIG. 17 shows changes in flow velocity with respect to time measured at a certain sampling point in each scanning line. The measured results for the 1st scanning line, 2nd scanning line, . . . , 8th scanning line are depicted in sequence from above.

The time taken to transmit/receive ultrasonic waves for one scanning line is given by $$200\ \mu s \times 16 = 3.2\ ms$$

The time taken to scan one frame is given by $$3.2\ ms \times 8 = 25.6\ ms$$

It will thus be understood that velocity data at one sampling point is obtained every 25.6 ms and there is a time difference of 3.2 ms between the sampling point on each scanning line and the sampling point on the next adjacent scanning line.

Figure 18:
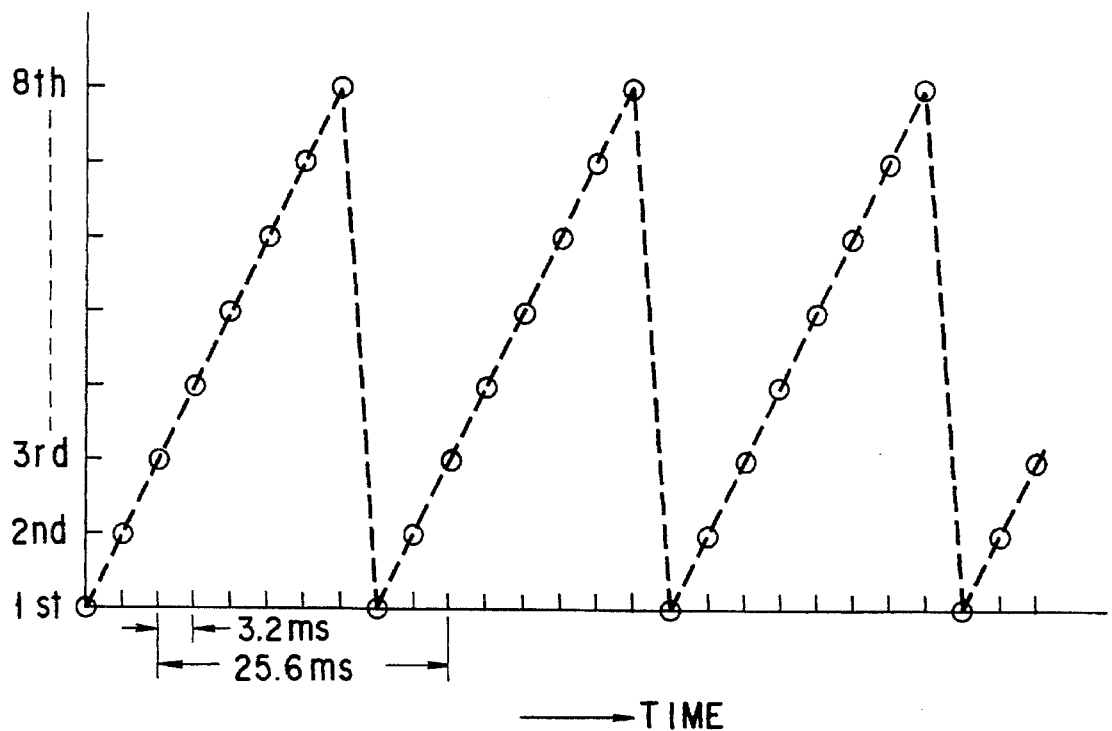
FIG. 18 a diagram illustrating the time difference between the data items measured of scanning lines and also the time difference between the data items measured of frames.

FIG. 18 is a diagram more clearly illustrating the time difference between the data items measured of scanning lines and also the time difference between the data items measured of frames. Plotted on the abscissa is time, and plotted on the ordinate is scanning lines. Mark "o" indicates the time at which the data on a scanning line is acquired.

Figure 19:
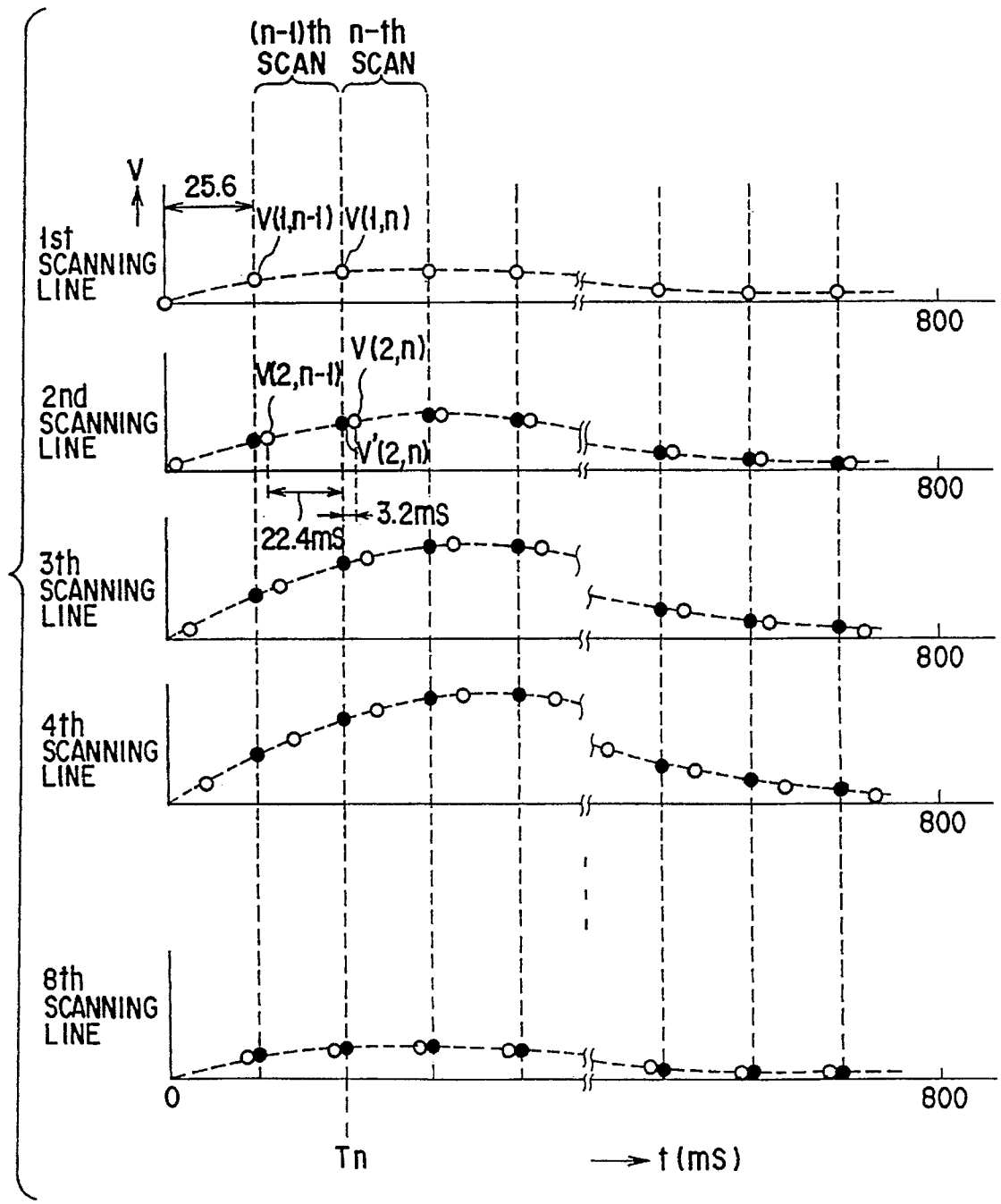
FIG. 19 shows changes in measured value and interpolated value of blood flow velocity with respect to time for each scanning line.

In FIG. 19, which corresponds to FIG. 17, measured velocity values are indicated by white dots, while time-interpolated velocity values are indicated by black dots. Here, the unified time to which the times of data acquisition at all the sampling points are to be unified is defined as the time at which data is acquired in the 1st scanning line. It should be noted that the unified time has only to be the same for all the sampling points and hence any other time may be selected to be the unified time.

The method by which the second time-interpolation calculation unit 36 obtains velocity values at the unified time will be described below. The time-interpolation method by the first time-interpolation calculation unit 35 is the same as that by the second unit 36. Any one of currently used interpolation techniques, such as linear interpolation, sink interpolation, etc., may be used. Here, the time interpolation will be described taking linear interpolation by way of example.

Suppose that the flow velocity measured at the sampling point on the i-th scanning line in the (n−1)st scan is V(i, n−1), the velocity value measured at the same sampling point in the n-th scan is V(i, n), the time interval from the time of acquisition of V(i, n−1) to the unified time Tn is ΔT1, the time interval from the unified time Tn to the time of acquisition of V(i, n) is ΔT2, and the period of measurement of flow velocity at the sampling point is ΔT (=ΔT1+ΔT2). Then, the interpolated value V (i, n) to be obtained will be given by $$V'(i,\ n) = V(i,\ n-1) \times (\Delta T2/\Delta T) + V(i,\ n) \times (\Delta T1/\Delta T)$$

That is, the interpolated value at the unified time in the n-th scan is obtained from the measured value in the (n−1)st scan and the measured value in the n-th scan. As a specific example, the interpolated value V'(2, n) for the second scanning line of FIG. 19 is given by $$V(2,\ n) = V(2,\ n-1) \times (3.2/25.6) + V(2,\ n) \times (22.4/25.6)$$

The interpolated value thus obtained is used to calculate the flow rate.

Figure 20:
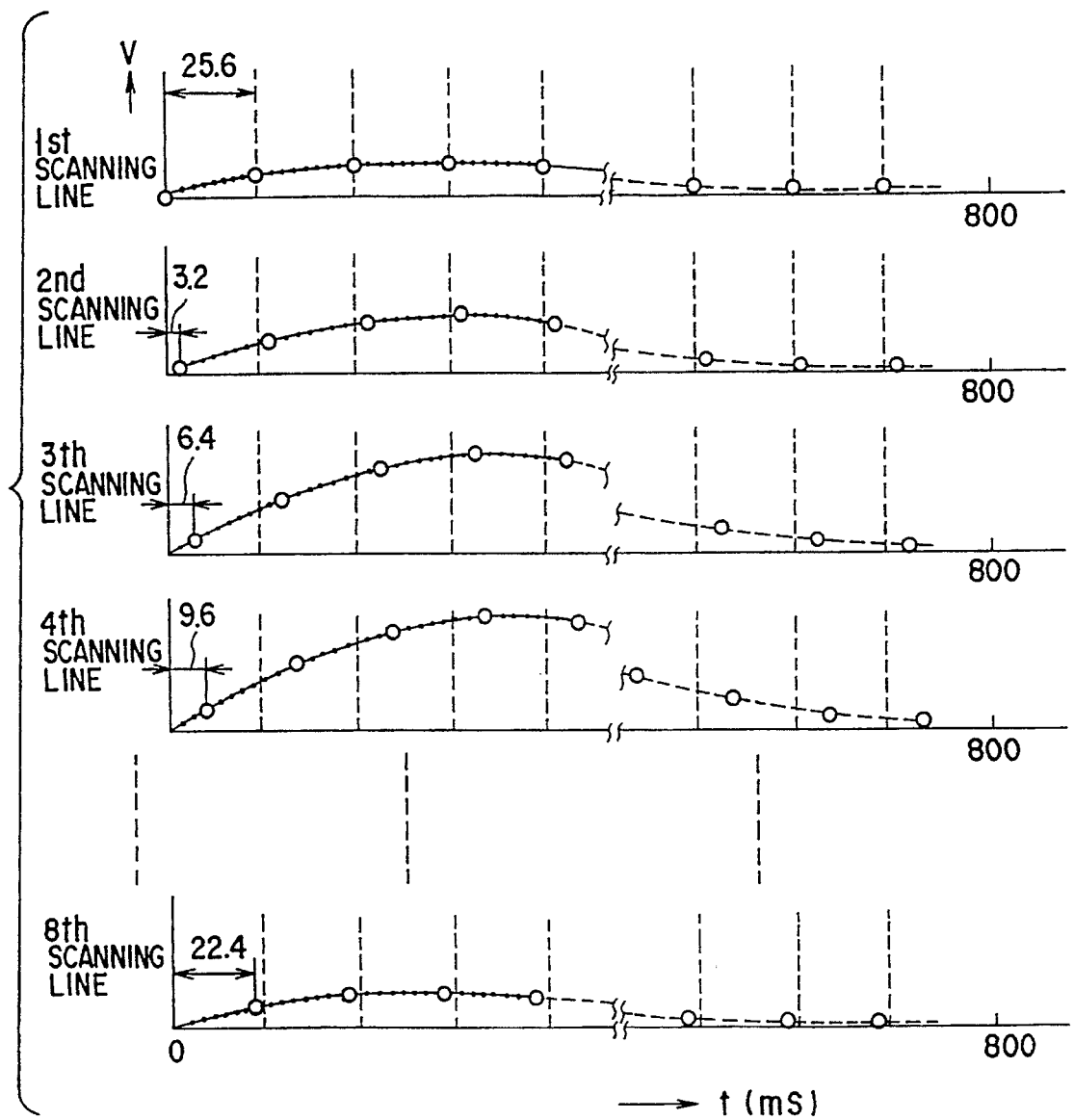
FIG. 20 shows changes in measured flow velocity value and interpolated flow velocity value obtained at short intervals for each scanning line.

FIG. 20 shows an example in which interpolated values are obtained at intervals of a much shorter time. In this case, data are obtained at intervals of 3.2 ms in each scanning line. In the case of FIG. 19, data are obtained at intervals of 25.6 ms in each scanning line. In the case of FIG. 20, therefore, eight times as much data is obtained as compared to the data obtained in FIG. 17, thus improving time resolution.

In the above, although the time compensation technique has been described in terms of flow rate measurement, it may also be used for displaying a tomography image and a velocity image, power Doppler image and a tissue Doppler image in real time. That is, images may be displayed on the basis of interpolated values. The blood flow velocity display, which is known as color Doppler, has already been used clinically. In general, in the flow velocity display, the number of transmissions of ultrasonic waves for each scanning line is reduced and the number of scanning lines is increased in comparison with the flow rate measurement, thus checking a reduction in time resolution and enlarging the field of view. For example, suppose that the number of transmissions for each scanning line is eight, the number of the color-Doppler scanning lines is 32, the number of the B-mode scanning lines is 64, and the rate frequency is 5 KHz. Then, the time taken to make one frame of scan will be $$T = (8 \times 32 + 64)/5\ KHz = 64\ ms$$

Thus, for each of 32 color Doppler scanning lines, data is obtained at intervals of 64 ms. In the example of FIG. 20, for 32 scanning lines, interpolated values are obtained every 64 ms/32=2 ms. By using data kept in time coincidence, an image free of time differences can be displayed smoothly at a high time resolution. In the so-called multi-directional simultaneous reception in which reflected waves are received from multiple directions for each transmission of ultrasonic waves, the waves may be regarded as having been generated at the same time. In the case of two-direction simultaneous reception, in the above example, one frame of flow velocity image will be composed of 64 scanning lines. Not only the velocity of the blood flow, but also the velocity of the tissue such as the cardiac muscle may be obtained by utilizing Doppler effect thereby to display the velocity in the form of a two-dimensional color image and to output the measured value of the velocity.

In the conventional method called color Doppler, blood flow information (velocity, variance, power, etc.) is displayed in real time. In one frame of image, the time phase varies with the scanning lines. In an extreme case, there is the possibility that forward flow and backward flow may be displayed simultaneously as opposed to actual phenomena. According to the present embodiment, however, this problem is resolved by using values kept in time coincidence. Moreover, by interpolation a large number of items of data and hence more frames can be obtained, thus permitting continuous, smooth display. Furthermore, since information is stored temporarily in the memory for calculation and images are displayed repeatedly, the doctor can observe medical phenomena calmly. In addition, since the number of frames can be increased, more-detailed dynamic observations can be made, which is very useful in diagnosis.

Although the preferred embodiments of the present invention have been disclosed and described, it is apparent that other embodiments and modifications are possible.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnosis apparatus comprising:
   a probe to be set in contact with a subject under examination, for transmitting ultrasonic waves and receiving reflected waves;
   scanning means for driving said probe to scan a sectional plane of the subject with an ultrasonic beam;
   means for obtaining tomography data from an output of said scanning means;
   means for obtaining velocity data from the output of said scanning means;
   first storage means for storing multiple frames of the tomography data;
   second storage means for storing multiple frames of the velocity data;
   display means for displaying the tomography data stored in said first storage means as a tomography image after said scanning means finishes scanning the sectional plane;
   operating means for setting a region of interest (ROI) on the tomography image displayed by said display means; and
   means for calculating, for each frame, one of a distribution of blood flow velocity, a blood flow rate and a tissue velocity from the velocity data stored in said second storage means and corresponding to the ROI.

2. The apparatus according to claim 1, further comprising third storage means for storing scan area data representing a scan area from which the velocity data is obtained, and in which said display means displays a marker formed from the scan area data to indicate the scan area, or a color velocity image formed from the velocity data, superimposed on the tomography image.

3. The apparatus according to claim 1, wherein the tomography data and the velocity data are stored in said first and second storage means, respectively, in association with a data item representing a time at which the tomography data was acquired and a data item representing a time at which the velocity data was acquired.

4. The apparatus according to claim 1, further comprising means for providing and storing electrocardiogram data, wherein the tomography data, the velocity data and the electrocardiogram data are stored in association with a data item representing a time at which the tomography data was acquired, a data item representing a time at which the velocity data was acquired, and a data item representing a time at which the electrocardiogram data was provided.

5. The apparatus according to claim 4, wherein said first storage means includes means for storing said tomography data for multiple frames corresponding to at least one heart beat period, and said second storage means includes means for storing said flow velocity data for multiple frames corresponding to at least one heart beat period.

6. An ultrasonic diagnosis apparatus comprising:
   a probe to be set in contact with a subject under examination, for transmitting ultrasonic waves and receiving reflected waves;
   scanning means for driving said probe to scan a sectional plane of the subject with an ultrasonic beam;
   means for obtaining tomography data from an output of said scanning means;
   means for obtaining velocity data from the output of said scanning means;
   display means for displaying the tomography data as a tomography image;
   operating means for setting a region of interest (ROI) on the tomography image displayed by said display means; and
   means for calculating, for each frame, one of a distribution of blood flow velocity, a blood flow rate and a tissue velocity from the velocity data,
   wherein said display means displays a graph showing how the blood flow rate changes with time, and displays a marker along a time axis of said graph, said marker being displayed in a position corresponding to a time phase of said tomography image being displayed.

7. The apparatus according to claim 6, further comprising input means for shifting the display position of said marker, and said display means includes means for displaying the tomography image of a time phase corresponding to the position of said marker.

8. The apparatus according to claim 6, wherein said display means displays flow velocity profiles for the ROI, the flow velocity profiles differ in time phase and are arranged according to a sequential order of the time phase.

9. An ultrasonic diagnosis apparatus comprising:
   a probe to be set in contact with a subject under examination, for transmitting ultrasonic waves and receiving reflected waves;
   scanning means for driving said probe to scan a sectional plane of the subject with an ultrasonic beam;
   means for obtaining tomography data from an output of said scanning means;
   means for obtaining velocity data from the output of said scanning means;
   display means for displaying the tomography data as a tomography image;
   operating means for setting a region of interest (ROI) on the tomography image displayed by said display means; and
   means for calculating, for each frame, one of a distribution of blood flow velocity, a blood flow rate and a distribution of tissue velocity from the velocity data corresponding to the ROI,
   wherein said display means displays, on one screen, the tomography image, a graph showing how the blood flow rate changes with time, and velocity profiles for the ROI, the velocity profiles differ in time phase and are arranged according to a sequential order of time phase parallel to a time axis of the graph.

10. An ultrasonic diagnosis apparatus comprising:
    a probe for transmitting ultrasonic waves and receiving reflected waves;
    scanning means for driving said probe to scan a sectional plane of a subject under examination, with an ultrasonic beam;

calculation means for calculating reflected wave data, for each of plural sampling points in a sectional plane of the subject, from an output of said scanning means;

storage means for storing at least two frames of the reflected wave data;

interpolation means for interpolating reflected wave data equivalent to reflected wave data acquired by scanning simultaneously all sampling points, from the reflected wave data stored in said storage means;

display means for displaying a two dimensional image obtained from the reflected wave data interpolated by said interpolation means.

11. The apparatus according to claim 10, wherein said reflected wave data is one of blood flow velocity data and blood flow rate data.

12. The apparatus according to claim 10, wherein said reflected wave data is one of power Doppler data and tissue Doppler data.

13. The apparatus according to claim 10, further comprising means for obtaining flow velocity profiles from the reflected wave data interpolated by said interpolation means and displaying the flow velocity profiles.

* * * * *